US010376142B2

(12) United States Patent
Dirghangi et al.

(10) Patent No.: US 10,376,142 B2
(45) Date of Patent: Aug. 13, 2019

(54) DEVICE AND METHOD FOR CAPTURING, ANALYZING, AND SENDING STILL AND VIDEO IMAGES OF THE FUNDUS DURING EXAMINATION USING AN OPHTHALMOSCOPE

(71) Applicant: Scanoptix, Inc., Charlottesville, VA (US)

(72) Inventors: Arjun Dirghangi, Charlottesville, VA (US); Gopal Metro, Charlottesville, VA (US); Dustin Williams, Kirkland, WA (US); Varundev Babu, Charlottesville, VA (US); Daniel Lagalante, Syosset, NY (US); Jeffrey Iris, Sammamish, WA (US); Ayush Sagar, Somerville, MA (US); Renat Badykov, Samara (RU)

(73) Assignee: Scanoptix, Inc., Charlottesville, VA (US)

( * ) Notice: Subject to any disclaimer, the term of this patent is extended or adjusted under 35 U.S.C. 154(b) by 0 days.

(21) Appl. No.: 15/892,286

(22) Filed: Feb. 8, 2018

(65) Prior Publication Data

US 2018/0220889 A1  Aug. 9, 2018

Related U.S. Application Data

(60) Provisional application No. 62/456,630, filed on Feb. 8, 2017.

(51) Int. Cl.
 *A61B 3/18* (2006.01)
 *A61B 3/00* (2006.01)
 (Continued)

(52) U.S. Cl.
 CPC .............. *A61B 3/185* (2013.01); *A61B 3/005* (2013.01); *A61B 3/0025* (2013.01);
 (Continued)

(58) Field of Classification Search
 CPC ....... A61B 3/185; A61B 3/0025; A61B 3/005; A61B 3/12; A61B 3/0033; A61B 3/156;
 (Continued)

(56) References Cited

U.S. PATENT DOCUMENTS

| 4,304,483 A | 12/1981 | Whitten |
| 6,149,273 A | 11/2000 | Matthews |

(Continued)

FOREIGN PATENT DOCUMENTS

| DE | 102010018 B4 | 7/2012 |
| DE | 102010018883 B4 | 7/2012 |
| EP | 0048181 A2 | 5/1986 |
| WO | 2006118560 A2 | 11/2006 |
| WO | 2012177544 A1 | 12/2012 |

OTHER PUBLICATIONS

Provizion Optics Brochure.
(Continued)

*Primary Examiner* — Jack Dinh
(74) *Attorney, Agent, or Firm* — Woods Rogers PLC; Nathan A. Evans

(57) ABSTRACT

The present invention is directed to a medical imaging device attachment with onboard sensor array and computational processing unit, which can be adapted to and reversibly attached to multiple models of binocular indirect ophthalmoscopes ("BIOs"), enabling simultaneous or time-delayed viewing and collaborative review of photographs or videos from an eye examination. The invention also claims a method for photographing and integrating information associated with the images, videos, or other data generated from the eye examination.

30 Claims, 12 Drawing Sheets

(51) Int. Cl.
- *A61B 3/12* (2006.01)
- *A61B 3/14* (2006.01)
- *A61B 3/15* (2006.01)
- *A61B 3/13* (2006.01)

(52) U.S. Cl.
CPC .............. *A61B 3/0033* (2013.01); *A61B 3/12* (2013.01); *A61B 3/132* (2013.01); *A61B 3/145* (2013.01); *A61B 3/15* (2013.01); *A61B 3/156* (2013.01); *A61B 2560/045* (2013.01); *A61B 2560/0475* (2013.01)

(58) Field of Classification Search
CPC ............ A61B 3/145; A61B 2560/0475; A61B 2560/045
See application file for complete search history.

(56) References Cited

U.S. PATENT DOCUMENTS

| | | |
|---|---|---|
| 6,393,431 B1 | 5/2002 | Salvati et al. |
| 7,883,210 B2 | 2/2011 | Filar |
| 2012/0200690 A1 | 8/2012 | Beasley |

OTHER PUBLICATIONS

Appasamy VIO-7 Video Indirect Ophthalmoscope Brochure.
Heine Omega 500 Indirect Ophthalmoscope with DV1 Digital Video Camera Brochure.
Keeler Vantage Plus LED Digital Brochure.
D-Eye Smartphone-Based Retinal Imaging System Brochure.
Neitz IO-a Brochure.
Volk In-View Website.
PCT/US18/17481 Search Report, Written Opinion, and prior art cited therein (11 pages).

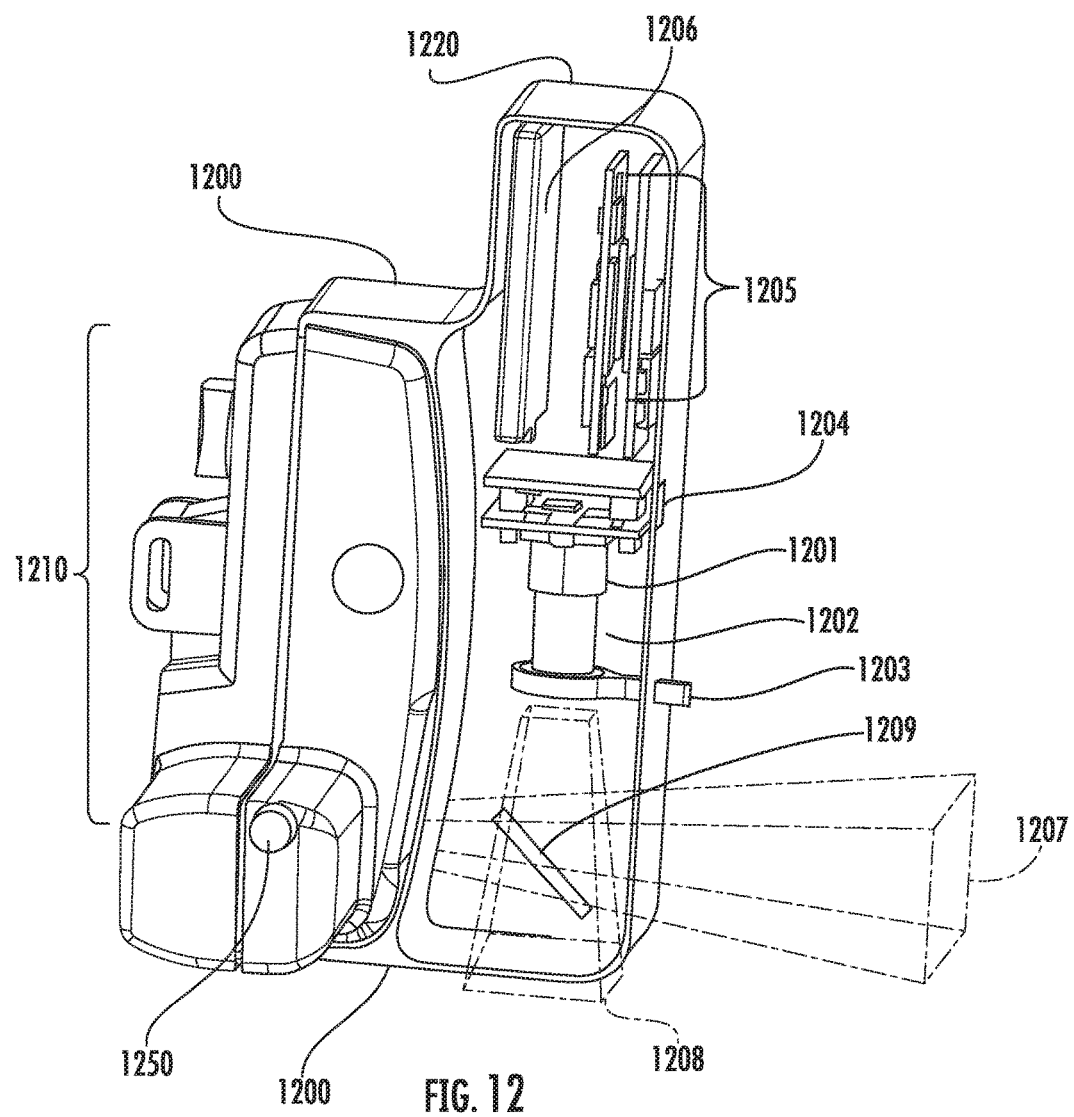

DEVICE AND METHOD FOR CAPTURING, ANALYZING, AND SENDING STILL AND VIDEO IMAGES OF THE FUNDUS DURING EXAMINATION USING AN OPHTHALMOSCOPE

CROSS-REFERENCE TO RELATED APPLICATIONS

The present application relies on the disclosures of and claims priority to and the benefit of the filing date of U.S. Provisional Application No. 62/456,630, filed Feb. 8, 2017. The disclosures of that application are hereby incorporated by reference herein in their entireties.

BACKGROUND OF THE INVENTION

Field of the Invention

The present invention is directed to a medical imaging device attachment with onboard sensor array and computational processing unit, which can be adapted to and reversibly attached to multiple models of binocular indirect ophthalmoscopes ("BIOs"), enabling enhanced diagnostic capabilities to ophthalmologists and optometrists beyond the traditional manual ophthalmic examination, such as wireless automatic capture and transmission of high-fidelity images directly from the perspective of a user performing an eye examination; while allowing the unimpaired, full use of the examination instrument via a custom form-fitted mechanical and optical design; and enabling simultaneous or time-delayed viewing and collaborative review of photographs or videos from said eye examination. The invention also includes an integrated system for onboard detection and enhancement of clinical imagery with ambient examination-related feedback to the user via visual and non-visual interactive notifications to aid in the diagnostic examination, as well as the coordinated collection, transmission, management, and maintenance of imaging and related metadata from ophthalmic examinations, and additionally allows for multi-user collaboration generated by one or more device(s) or networks of devices and multiple users.

Description of the Related Art

The state of the art prior to the invention taught herein was for manual binocular ophthalmoscopes and handheld lenses to view the human eye by a practitioner performing an eye examination, specifically a large portion of the fundus (i.e., the retina, vitreous, and optic nerve). Given the optical properties of indirect ophthalmoscopy, the examiner is required to mentally invert the observed retinal image upside down and backwards to determine the correct orientation and location of observed findings, with rapidly-shifting focus, significant glare, subtle tilting of the handheld lens, and small shifts in patient gaze and lighting conditions often resulting in a fleeting, limited, and distorted views of the fundus and repeated, lengthy, and uncomfortable examinations for the patients in order to verify possible clinical observations through pharmacologically dilated pupils with intensely bright light from the ophthalmoscope. These prior art instruments, moreover, were purely optical, manual instruments, and unable to capture photographs or videos in real-time during the patient examination. Recording clinical observations into the patient medical record with such prior art instruments requires the examiner to manually draw an artistic representation of findings as they recall their appearance (while inverting and reversing the optical appearance of findings through the instrument), or describing such observations in text form. This leads to poor quality of care, due to the inherent limitations of the traditional fundus exam as discussed above, which require technical staff availability and separate imaging devices typically located outside the doctor's examination room (which may or may not be readily available) in order to conduct clinical photography of the eye.

More recently, a wired video indirect ophthalmoscope has been described and produced, allowing for digital transmission of photographs concurrent with the patient examination. However, in practice, these instruments typically require two people to conduct such operation, including manually focusing and aiming the onboard camera to better align the imaged area with the doctor's view; and managing a wired USB connection to a computer device as well as a separate wired connection to a footswitch controller to trigger image or video capture (thus tethering the physician to both computer and footswitch, and posing a usability challenge and potential safety hazard in a dynamic clinical examination which requires significant movement and repositioning of the examiner fully around on both sides of the patient to examine both eyes in all gazes of view); along with requiring the simultaneous operation of image management or video editing software with the examiner and assistant having to refer dynamically to video output on a separate screen while the field of view of the examiner is largely taken up by the ophthalmoscope's viewing eyepieces, all greatly diminishing the usability and practicability in practice during the patient examination, particularly in the common circumstances in which such trained assistants are not available during the fundus examination. The inherent usability concerns and additional personnel requirements of such systems have greatly hindered such video ophthalmoscopes' usage and spread in eye care and limited the public health benefits of concurrent digital documentation of eye examinations. Additionally, the optical arrangement of key components in such prior devices use two or more triangular reflecting mirror blocks enclosed in the instrument straddling adjacent to the central visual axis of the instrument's optical system, in coordination with a centrally-positioned beamsplitter (partially-reflective mirror) in between the two triangular mirror blocks. The centrally-positioned beamsplitter or prism (such as a pentaprism) reflects the central imagery towards a centrally-positioned camera, but the two adjacent triangular mirror blocks reflect adjacent imagery towards each respective eyepiece. As such, the optical system bears significant complexity of design, and importantly, the centrally-positioned beamsplitter or prism may partially or totally occlude portions of the imagery relative to the laterally-located optical pathway to the instrument eyepieces, and cannot in all circumstances ensure good correspondence between camera and examiner views. As a result, this requires additional mechanical elements to more closely align the camera view with the examiner's view. However, the examiner's view is nearly totally occluded by the instrument eyepieces. Additionally, in many instances, the eyepieces include low-plus spherical lenses (such as +1.50 or +2.00 diopters) to allow a presbyopic examiner to comfortably view the aerial image of the examined retina through the handheld lens used in indirect ophthalmoscopy. In these situations, switching one's view through the instrument eyepieces to an off-instrument display screen rapidly to guide the assistant or independently attempt to adjust instrument controls to improve device-instrument correspondence, adjust video or image recording or playback using onscreen controls, or interact with software user interface elements on an external or even adjacent display may be uncomfortable or disorienting for the examiner. As such, the examiner of such instruments requires an assistant to manually adjust the camera view using such additional mechanical adjustments such as dials or levers using an off screen display, close communication with the examiner, and a process of trial and error to minimize the discrepancies between the examiner and camera views. Furthermore, the mechanics and optical elements of prior art devices, including the imaging capabilities, are fully enclosed in the ophthalmoscope, requiring the user to purchase an entirely new ophthalmoscope machine with such capabilities to conduct clinical examinations with the option of digital photography/videography, therefore further limiting the practicability of greater adoption, because the majority of users already have purchased and are trained and independently using traditional, non-digital imaging ophthalmoscopes in their practices. Also, in other designs, the prior described instruments require partial or complete disassembly or other modifications of the external enclosure of the existing ophthalmoscope in order to accommodate a proposed retrofitted attachment camera with a securely aligned mounting assembly, or require additional mounting hardware and special tools for installation such as mounting pins, screws, or other invasive elements, which may be impractical for most users, may damage the users' purchased instruments, and may potentially void the warranties or service agreements for users' existing instrument purchases. Additionally, the great expense of previous video ophthalmoscopes (on a par with benchtop fundus cameras) typically only allows for installation in one examination lane for a typical ophthalmic practice, not only providing inferior quality images than a benchtop fundus camera due to inherent limitations in indirect ophthalmoscopic image quality as well as previously-discussed limitations, but also requiring the physician to capture all images (technicians are typically not trained in indirect ophthalmoscopy) and representing a bottleneck in the clinical workflow of a modern ophthalmology or optometry practice, as all patients in a typical multi-lane setting to be imaged would have to be redirected to a specific examination lane following a traditional examination.

The remaining alternatives other than an ophthalmoscope with an embedded camera in order to obtain clinical photography are in using traditional benchtop fundus cameras and scanning laser ophthalmoscopes, both of which are expensive, bulky, and require the use of a trained retinal photographer. Nonmydriatic fundus cameras and scanning laser ophthalmoscopes, which do not require the pharmacologic dilation of the patient's pupil, can incentivize physicians to not dilate their patients, and thus not examine the retinal far periphery; however, nonmydriatic fundus photographs routinely produce image artifacts which can be read as false positives for alarming features such as retinal detachments and posterior segment tumors, while being unable to examine the retinal far periphery, disincentivizing eye physicians from conducting a complete dilated examination of the ophthalmic fundus and leading to inferior quality care. Additionally, communication gaps between eye physicians and retinal photographers routinely limit the quality and accuracy of images actually obtained in clinical practice, and staffing and patient scheduling gaps limit whether photography can be conducted at all using such technician-performed techniques. Smartphone and other mobile camera systems are alternatives to the fixed fundus camera, but face relatively poor patient acceptance, are often cumbersome to use (particularly in focus and exposure control), require yet another proprietary device to capture photographs redundant to the retinal examination, and typically also cannot adequately capture the retinal periphery. The present invention promotes the gold standard technique for retinal examination and the only technique allowing for dynamic examination of the full retinal periphery (indirect ophthalmoscopy), as recommended by both optometric and ophthalmology professional bodies, and the added benefit of simultaneous capture and redisplay of fundus photography and video, using the same existing examination instruments doctors already possess, are trained upon, and are comfortable using, allowing for augmented retinal examination without introducing a separate step in clinical image acquisition beyond the doctor's own examination process.

Moreover, neither of the aforementioned options—traditional benchtop fundus cameras and scanning laser ophthalmoscopes—are capable of imaging the full periphery of the retina where many retinal detachments and several kinds of posterior segment tumors originate—this is something only indirect ophthalmoscopes are currently capable of fully viewing (e.g., the retinal far periphery), in combination with dynamic fundus examination procedures familiar to ophthalmologists and optometrists, such as scleral depressed examination techniques, which can be performed in concert with other diagnostic and therapeutic maneuvers such as fluorescein angiography, scleral indentation, and indirect laser photocoagulation.

SUMMARY OF THE INVENTION

A core problem solved by the current invention is in gaining the ability to seamlessly take clinical photographs with a high degree of fidelity from the ophthalmic fundus examination—in a preferred embodiment, of the pharmacologically-dilated eye of a patient—taken by the user using the standard examination instruments they have already purchased and have been trained to properly use in their routine clinical practice, with the free and full use of all existing settings and onboard BIO instrument illumination and view-related controls, with minimal or no modifications or alterations necessary in the examiner's routine examination technique, and no damage or disassembly of their examination equipment necessary for the reversible mounting and secure positioning of the camera and computational apparatus. The current invention also encourages the gold-standard examination technique of the retina—indirect ophthalmoscopy—and makes possible seamless wireless transmission of clinical photographs and videos from the clinical examination to other viewers such as students or other practitioners, for training, patient care, clinical research, telemedicine, and feedback during or after an examination, via integrated onboard and off-device networked computational and software elements. This transforms the traditional manual fundus examination into an augmented image-guided examination, allowing the doctor and patient the benefits of clinical photographic documentation and enhancement, while optimizing workflows.

Improvements over the prior art include, but are not limited to, the ability for the user to simultaneously capture ophthalmic features manually; automatic device capture of images integrating onboard integrated sensors, computational processing capabilities, and tightly-integrated on-device and off-device algorithmic processing of imagery; allowing for feature recognition of the eye and ocular features of interest; and/or automatically montaging multiple overlapping images to more broadly map and redisplay the ocular features via networked software programs; all included in a very small, integrated form factor such that the claimed device can be self-contained and reversibly mounted by the user on a pre-existing ophthalmoscope without specialized training or tools—and without procuring a new ophthalmoscope, and without damaging or directly modifying the preexisting instrument. In other words, the presently taught device allows an existing ophthalmoscope to be retrofitted with a mobile embedded imaging system to make it an imaging device with wireless capture and transmission capabilities, in preferred embodiments, and it can be implemented by the user without having to obtain a new ophthalmoscope. The device taught herein improves upon prior optical design by simplifying the optical system by requiring only one centrally-positioned triangular reflecting mirror block (as is typically found inside the optical system of most BIOS) and an onboard linear plate beamsplitter, not requiring a prism or laterally-located mirror blocks; as opposed to two or more laterally-positioned mirror blocks in coordination with a prism (such as a pentaprism) or centrally-positioned or laterally-positioned beamsplitter, which ordinarily may totally or partially occlude the optical pathway to the instrument eyepieces. Such prior configurations introduce significant device complexity to the mechanical design and opportunities for distortion of imagery, and cannot ensure consistent correspondence between camera and examiner views in many examination scenarios. The optical system here described allows for a greater fidelity of correspondence between onboard camera and examiner views over a much-greater breadth of examination scenarios. In one embodiment, a mechanical adjustment lever allows for customization of the optical system by tilting, in a coplanar relationship, the beamsplitter mirror and embedded camera assembly, to permit a greater range of examiner wearing patterns of the instrument, such as physicians who wear the instrument at a significant downward tilt to examine patients significantly below their eye level, or physicians who wear spectacles. In another embodiment, the use of a wider field of view camera lens, along with a high-resolution camera sensor, may be used to customize the viewing angle of the captured imagery to the preferred instrument viewing position of individual users, by setting the desired viewing region by cropping out extraneous imagery via a software interface. In one instance, this software-enabled field of view image crop control may be used in combination with an initial user calibration procedure using, but not requiring, the use of a standardized target to allow for automatic configuration of the camera view—without requiring interaction with the onboard mechanical device controls such as adjustment levers or dials.

Beyond its optical properties, the device and integrated system described also allow for subsequent review and enhancement of ocular imagery beyond the range of view ordinarily visible or accessible to the otherwise unaided eye of the examiner using their existing manual BIO instrument. The apparatus thus permits the routine use of image-guided augmented examination for improved patient care, enhanced detection and documentation of clinical pathology, and serial comparison of follow-up findings, as well as improved practice efficiencies by the simultaneous dual use of BIO instruments for both examination and enhanced clinical imaging purposes.

The design allows for transmission of data, an image trigger that automatically captures when certain features are present in the ophthalmoscope's viewfinder, manual focus, closed-loop and open-loop autofocus, and other optical and sensor-assisted algorithmic techniques such as focus stacking, software-selectable focus planes, expanded depth of field imaging, and region of interest (ROI)-based focus and exposure controls to ensure crisp focus and exposure without or with minimal user intervention in routine clinical examination settings, image enhancement, automatic montaging to see more complete pictures of, for example, the retina, and annotation of findings. Focus stacking is similar to expanded depth of field imaging; also known as focal plane merging and z-stacking or focus blending; it is a digital image processing technique which combines multiple images taken at different focus distances to give a resulting image with a greater depth of field (DOF) than any of the individual source images. Focus stacking can be used in any situation where individual images have a very shallow depth of field, such as encountered in indirect ophthalmoscopy. Unlike existing prior art, in one embodiment, no display screen (either on-device or off-device) is required to be referenced during examination sessions for clinical findings to be imaged with high fidelity, as focus, exposure, and field of view are all faithfully maintained by the design of the device. Though one prior art system describes review of images on the device itself on a display screen either attached or located adjacent to the viewpiece or handheld, given that the indirect ophthalmoscope viewpieces themselves inherently occlude and take up most of the examiner's field of view, referring to any external display screens while actively examining a patient is quite difficult in practice. For this reason, no external or on-device display screen is required in this device design, and device notifications are designed to occur "ambiently," that is, without obstructing or minimally obstructing the examiner's view, not requiring the examiner to alter their gaze during the clinical examination and still receive examination- and device status-related interactive notifications. All of these capabilities are enabled by the same device mounted on an existing instrument with minimal user intervention. Ambient notifications include, but are not limited to, light feedback, sound feedback, haptic feedback, touch feedback, vibrations, buzzes, clicks, noises, beeps, or speech, or any other notification or feedback that does not interfere with the examiner's examination of the patient's eye, such as by occluding or obstructing the examiner's view or otherwise distracting the examiner or limiting the examiner's movement.

Software-selectable focusing planes are an algorithmic and optical set of techniques in which one or more focal planes can be selected from one or more electronically-controlled cameras, lenses, or image sensors, in which, in a preferred embodiment, an electronically-adjustable focal length can be selected or tuned electronically for an electronically-tunable lens, or desired focal length can be selected from an array of cameras adjusted to a variety of focal lengths, to optimize focus of the images/video captured by the device to the working distance between instrument and handheld condensing lens used by the examiner. In a preferred embodiment, these functions can be performed without the user having to resort to manual adjustment to mechanical levers, dials, or switches, to improve ergonomics, enhance operational workflow, and minimize or eliminate the need for an assistant to adjust the focus manually for individual users or examination parameters in which the lens may be held at a shorter or longer distance than typical. Additionally, the use of such techniques may enable, in one aspect, greater functionality of the device beyond the typical usage, in which the user can easily switch between a variant focal length or combination of focal lengths to enable in-focus image/video capture of structures in the anterior segment of the eye or around the eye, with or without the need for an additional examination lens, and then switch back to normal imaging modes to focus upon the aerial image of posterior segment ocular structures as imaged through the handheld condensing lens.

Expanded depth-of-field imaging is an algorithmic and optical set of techniques in which one or more electronically-controlled cameras, lenses, or image sensors with different imaging characteristics (most typically, cameras with varying focal lengths and f-numbers/apertures) are used in combination to algorithmically join multiple images captured at varying focal lengths into a composite image or images capturing a higher depth of field image with higher image quality given limited or varying ambient light than would ordinarily be captured by using one camera or sensor in isolation.

Region of interest-based imaging is an algorithmic and optical set of techniques in which certain preferred areas of the image(s) or video captured by the image sensor(s) to set global imaging settings (including, but not limited to, focus, exposure, white balance, and image trigger control) can be reprogrammably controlled by the user via a text- or graphical user interface on a separate networked computing device, or pre-set to minimize the need for user intervention. In certain aspects, additional image processing and computational image recognition techniques may be used including, but not limited to, recognition of certain ocular structures or abnormal or normal clinical findings, to dynamically set or change associated imaging parameters with minimal need for user intervention.

Use of onboard communications/telemetry transmission embedded in the device allows for multiple options for off-device transfer of data for reviewing, filing, and displaying clinical images and video. For example, this includes quick image review on a mobile device, simultaneous re-display on a tethered or untethered, networked video monitor (e.g., by Bluetooth, WiFi, radio frequency, or Internet connection), remote review by a supervising physician or other permitted third party, remote analytics data collection, concurrent sharing of clinical images and video with consulting practitioners (e.g., specialists), and seamless generation of imagery and clinical metadata which can be scrubbed (manually or automatically/algorithmically) of protected health information and patient identifiers to quickly generate large datasets of clinical imagery and physician practice patterns, suitable for data science applications for continuous quality improvement, such as machine learning, artificial intelligence and process automation in healthcare applications, and clinical research purposes. The device and integrated system can enable wired or wireless direct transmission to electronic medical record systems and point-of-care billing by an examining practitioner, and concurrent point-of-care sharing of clinical images/video to patient and families of patients for medical education and facilitating continuity of care. Onboard networked computational processing capabilities allow, in one embodiment, the off-device automatic recognition of or manual account login of authorized users of the device, automating the process of linking examining physicians to clinical imagery data for examined patients, examination sessions, and location. In one instance, such networked sensors would allow for automatic user recognition, authentication, and tagging of generated imagery in an examination session via an NFC or other wireless token carried by an authorized user, a securely paired smartphone, or via a QR code identification tag that, in one embodiment, would be recognized via computer vision algorithms, using the onboard camera or cameras and embedded microprocessor. Integration of onboard sensors, networked antennas, and embedded camera or cameras along with on-device and networked software can allow for simple, contactless wireless network configuration and coordination of multiple instances of the taught device within a clinical setting. The tight integration of the taught device hardware to reprogrammable on-device software and off-device software allows for a greatly improved user experience, improves usability, and enables a better-quality clinical examination beyond prior art hardware-only approaches. The device and system allows for augmented clinical examination facilitating review of images/videos by the practitioner without unnecessary discomfort to the patient following dilated examination, as the current clinical practice necessary to produce fundus photography on a routine basis usually requires repeat serial flash photography through the dilated pupil subsequent to or prior to the separate DFE (dilated funduscopic examination, which is conducted separately by the examining ophthalmologist or optometrist), as conducted using a dedicated large benchtop fundus camera by an ophthalmic technician in typically a physically separate clinical area from the examiner's medical examination room. As outlined earlier, practitioners performing the examination must remember what they see and then either verbally describe or draw a crude picture (either by hand, or using a rudimentary painting application) of what they observed based on their memory. The device will decrease the time necessary for such examinations (which are typically both inconvenient and uncomfortable for the patient), wait time for patients currently forced to wait for the availability of examining physicians as well as trained technicians to capture fundus photographs, and substantially reduce the possibility of human error due to potential for error inherent in clinical examination and documentation methods reliant solely upon human memory and physician documentation.

In one aspect, for those models of BIO instruments with LIO (laser indirect ophthalmoscope) functionality, the attachment/adapter system described allows simultaneous capture and remote redisplay of imagery, as well as feature recognition/augmented examination and treatment (such as guiding the ophthalmologist as to the size and region of the fundus to be treated with laser photocoagulation, the region already treated, and tracking stability vs. progression of pathology beyond previous regions of laser treatment. The system also allows for remote collaboration (real-time or delayed collaboration) for laser surgical procedures (in one application, for redisplay of barrier laser photocoagulation of retinal breaks to help guide the laser surgical procedure) for clinical documentation, telemedicine consultation, and medical education purposes.

In another aspect, the device can be reversibly attached to an existing ophthalmoscope by a practitioner or other untrained individual. In one embodiment, the device comprises a self-contained system comprising one or more cameras, a beam splitter (e.g., a partially reflective mirror) that is at a 45-degree angle to the incoming optical rays and the examiner so that the image being viewed by the examiner is the same or nearly the same as the image viewed by the camera, one or more antennas for wirelessly transmitting data to connect the device with one or more external devices (e.g., a computing device), user accessible memory, and a battery. The device also comprises, in one embodiment, a custom-fit bracket to attach the device to an ophthalmoscope. In one aspect, the device is positioned vis-à-vis the ophthalmoscope with the bracket (in one aspect, with adjustability) to allow the optics of the beam splitter and camera assembly to fit flush (or close to flush) and aligned (or close to aligned) with the external view port of the ophthalmoscope and aligned (or partially aligned) with the examiner's view; in this embodiment, the camera or cameras are located in between the eyepieces of the examination instrument and unlike in some prior art designs, is not dependent upon or limited by the field of view from only one of the binocular eyepieces. In one embodiment, two or more cameras may be used to enable a three-dimensional or high-dynamic range view. One or more brackets may be included to adapt to several types of ophthalmoscope models. The design of these brackets allows for full (or close to full) adjustment and operation of all BIO controls and unoccluded (or nearly unoccluded) passage and adjustment of optical imagery to the examiner as well as illumination from the BIO instrument to the patient's eye under examination. The device design does not require any onboard illumination source, but rather allows unobstructed (or nearly unobstructed) transmission of light and manipulation of the BIO illumination source. In one embodiment, the design of the brackets, embedded camera or cameras, and optical system relative to the examination viewing window at the front of the ophthalmoscope further allows for selectable or tunable alignment of the optical system and field of view by the user to accommodate ergonomic usability by the user, accommodate eyeglass correction by the examiner, and tilt and positioning of the ophthalmoscope on the examiner's head while reproducing imagery with a high degree of fidelity to the examiner's view. The battery and power management system may be tethered by wire or incorporated in the device enclosure fully, and may be user accessible for easy replacement while in use ("hot swapping") for extended examination periods between charging. The device also comprises a microprocessor, with connected communications antenna system consisting of one or more types of wireless antennas, as well as an integrated sensor array. In one aspect, the processor elements may comprise a reprogrammable system on a chip (SOC) or system on module (SOM), with one or more custom carrier PCBs (printed circuit boards), running the on-device software taught herein, bidirectionally communicating with off-device networked elements and software, and comprising the non-optical functions of the device and integrated system described. The reprogrammability of the system in combination with bidirectional networked interface with other onboard or off-device software elements and external computing devices represent additional substantial improvements to the prior art and enable a host of additional functionality to the integrated system, such as herein described.

Image capture may be accomplished by an external foot switch, which may be wired or wirelessly connected to the device, such as through a paired antenna. The image may be captured by remote image trigger either by a hardware device controller, or an off-device networked software control paired to the specific instrument and examination session. For example, in a clinical education setting, a teacher may capture an image while a student is using the device to examine a retina to capture a desired image or images of a specific feature of interest. Also, using an image preprocessor, sometimes in coordination with the processor, and a miniaturized camera, in combination and connected with a second or more computing device(s) (e.g., a mobile phone or EMR computer), auto capture is enabled along with auto enhancement, and auto-analysis, using machine learning and computer vision techniques. Imagery (still and/or video) may be processed either on-device, or by using post-processing techniques on a more robust connected computing device (such as, but not limited to, mobile smartphone, networked server, cloud-connected array of servers, or desktop or portable computer), so as to decrease the bulk and power requirements of the described device. This innovation can be used to, in one embodiment, automatically generate a high-quality image library of the examination and of multiple serial clinical encounters over time for rapid cross-comparison and cross-reference of the images while partially or wholly automating much of the ordinarily labor-intensive process of manual association and filing of examination-specific elements or metadata such as the examining physician, patient, and date of service.

In the optical system of the device, in addition to the beam splitter, optical glare reduction techniques may be utilized, such as in one embodiment, the use of one or more linearly polarized plates with variable light transmission (e.g., a linear plate polarizer), which may be used to polarize the outgoing light from the indirect ophthalmoscope illumination source, as well as one or more additional linearly polarized plates located prior to the camera image plane (polarizing the incoming light beams comprising the image being captured by the embedded miniaturized camera system), to remove glare and other stray reflective distractions from the image optically, thereby resulting in a higher quality clinical image. These optical glare reduction techniques enabled by the physical design of the device optical system may be used in multiple combinations with, or without, the use of dynamic algorithmic image processing techniques to reduce glare, which are enabled by, in one embodiment, the onboard microprocessor, or, in another embodiment, off-device software hosted remotely, such as in the cloud, or on a local networked computing device.

In one embodiment, auto-capture comprises automatic algorithmic detection as to whether a retina and/or optic nerve (or other fundus feature) is in view and in focus. If that is the case, the camera will automatically take a picture with no user intervention. This technique can aid in the usability of the instrument, in which there may be a delay between the user observing a feature of interest, small movements of the eye under examination, and capture of imagery using a manual trigger, resulting of non-capture of the desired imagery. This circumstance can be further minimized by, in one embodiment, use of constant automatic rapid capture of a series of images held algorithmically in an onboard image storage buffer in the computational system, such that after a manual image trigger signal generated by the user, the desired image or images of interest can be selected subsequently upon review via networked off-device software, from an automatically generated library of session images for later storage and retrieval. Auto-enhancement means that image or video capture will be automatically enhanced, meaning the image will automatically normalize such features as contrast and color, and minimize glare from reflected illumination using dynamic algorithmic image processing techniques, and includes, but is not limited to, digital sharpening, contrast enhancement, and removal of glare and occluding elements, improving the quality of imagery beyond what the user is able to ordinarily see with an un-augmented examination instrument, and improving the ease of cross-comparison between individual images and between clinical imaging sessions. In one aspect, the image will be centered, a standardized crop or border will be placed around the picture, and image orientation marks will be added algorithmically via on-device or off-device software.

Auto-analysis includes, but is not limited to, automatic algorithmic detection, flagging, and measurement of clinical features of interest, and comparison with prior detected features for evidence of clinical stability versus change, as well as comparison with reference databases of normal and abnormal clinical features, using a variety of techniques including, but not limited to, computer vision, deep learning, and artificial intelligence. In one aspect, auto-analysis will occur using connected software to correlate clinical images with an external library or set of algorithms determining attributes such as which eye is being examined, or flagging optic nerve and retinal periphery, noting abnormal features detected by the system, all of which may aid in clinical examination upon review of the image(s). Though such techniques have been used for analysis of ophthalmic imagery using traditional fundus cameras separate from the eye physician's examination, in this embodiment, via close integration with a standard ophthalmic examination instrument—in this taught embodiment, the indirect ophthalmoscope—algorithmic image enhancement and machine vision would be possible in real-time or close to real-time directly from the clinical examination session itself, allowing the benefits of algorithmic image analysis of ophthalmic imagery in clinical decision-making directly at the point of care, thus greatly improving practice efficiency and the clinical potential of any one examination and clinical encounter. Auto analysis may also enable redisplaying image flags or algorithmically/computationally-generated metadata in multiple formats, such as, but not limited to, text or annotated images and video. In one embodiment, auto analysis can display its output by electronically transmitting metadata and clinical imagery to a connected EMR/EHR (Electronic Medical Record/Electronic Health Record) system or a separate connected computing device or application linked to a patient's electronic chart. In another embodiment, redisplay of auto analysis results can be accomplished by superimposing automatically-generated tags and/or graphical overlays illustrating areas of concern upon the captured imagery. Using pre- or post-image processing, the images taken during the examination process or generated from video capture, will automatically join photographs capturing adjacent regions of the fundus, synthesizing a montage map of the patient's fundus automatically with minimal or no user intervention, enabling cross-comparison of images between patient examinations and between patients. Such cross-comparison can also be conducted, in one embodiment, by quick point-of-care cross-reference to a normative or pathologic database of fundus imagery (still or video) to enable immediate or close to immediate reference of patient pathology to an external image library for augmented examination enabling substantially enhanced clinical utility of the dilated fundus examination by the use of augmented examination technology. This will make the examination shorter and more comfortable to the patient, while permitting the practitioner a longer time to subsequently study the fundus by and through the images captured by the device and integrated system, while allowing for an enhanced level of detail, image quality, and diagnostic decision-making aids beyond which would be ordinarily possible in un-augmented ophthalmoscopy.

The device also incorporates security features to maintain patient confidentiality, system integrity, and integration of the device, integrated system, and other connected devices into an existing secure information technology network for use in a clinical setting. Videos, images, and clinical metadata, clinical data, user account information, and any other associated telemetry data pertinent to the operation of the device or system(s) used in the clinical data network may be encrypted by the device itself, allowing for secure transmission of data to a trusted, approved user or group of users, and allowing for a hierarchical data trail to be generated for access and manipulation of clinical data. Physical tokens, passcodes, or connected "trusted devices" (in one embodiment, a trusted device is a device that has been securely authenticated to an authorized user) can be used, in one instance, in combination with onboard telemetry such as, but not limited to, networked antennas to automatically detect the presence, absence, and use of the system by a "trusted team member" (in one embodiment, a trusted team member is a user authorized to conduct a specified examination or procedure and authenticated within a particular clinical care provider system) and appropriately tag and file generated imagery and metadata with a hierarchical audit trail to maintain data integrity, automate the appropriate tagging and filing of generated clinical imagery and documentation, and maintain clinical data in compliance with relevant regulatory protocols for protected health information, as well as for clinical research data applications.

BRIEF DESCRIPTION OF THE DRAWINGS

The accompanying drawings illustrate certain aspects of some of the embodiments of the present invention, and should not be used to limit or define the invention. Together with the written description the drawings serve to explain certain principles of the invention.

FIG. 12 is a schematic diagram of a depiction of one possible embodiment of the device taught herein, including the BIO, mounting bracket, and optional optical cartridge.

DETAILED DESCRIPTION OF VARIOUS EMBODIMENTS OF THE INVENTION

Figure 1:
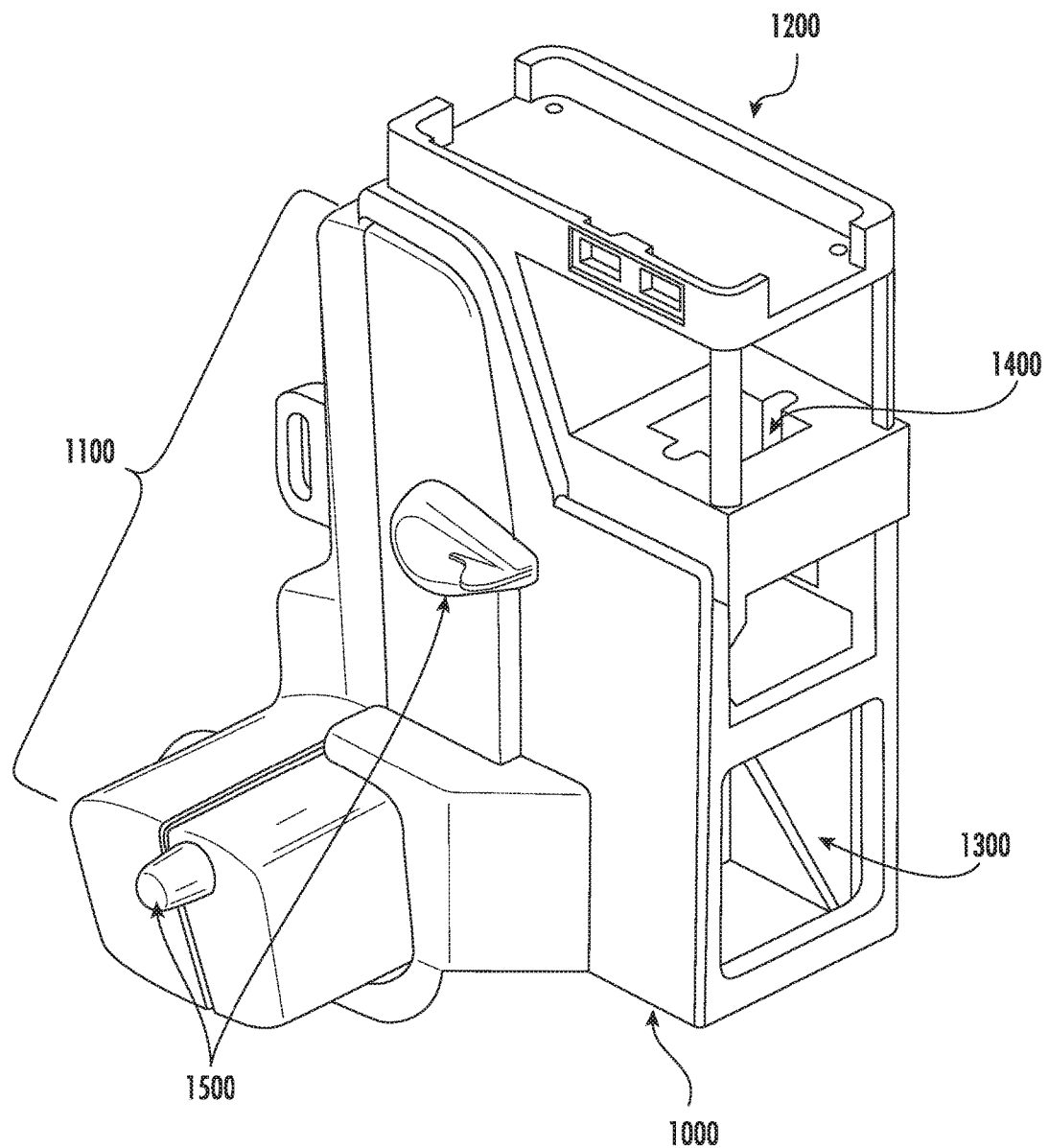
FIG. 1 is a schematic diagram of a depiction of one possible embodiment of the device taught herein, including the BIO, mounting bracket, and optional optical cartridge.

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Embodiments comprising various features may also consist of or consist essentially of those various features. Other embodiments of the invention will be apparent to those skilled in the art from consideration of the specification and practice of the invention. The description of the invention provided is merely exemplary in nature and, thus, variations that do not depart from the essence of the invention are intended to be within the scope of the invention. All references cited in this specification are hereby incorporated by reference in their entireties.

The hardware and system taught herein allows for the ability to semi-automatically or automatically generate fundus photographs and a live digital redisplay of the clinician's view (though not requiring an on-screen image for accurate image capture) during the conventional workflow of the eye exam itself, without requiring a trained technician or separate machine to do so. This allows for each patient examination lane to serve a dual purpose, as a combination patient examination and fundus photography/documentation station. The use of onboard and connected computing elements allows for the rapid automation of several elements previously requiring a dedicated technician or assistant, and physically separate image acquisition system (such as benchtop fundus camera), in order to acquire fundus photography/clinical documentation of the posterior segment examination of the eye in addition to the clinical examination of the eye by a qualified eye care physician. The ability to conduct a retinal exam and routinely obtain a concurrent image capture session and also enable a simultaneous, real-time, store-and-forward, or subsequent image review process, with no or almost no additional requirement for a technician or assistant to conduct the photography, in addition to increasing clinical practice efficiencies, should enhance the clinical review process, accuracy, and interpretation of the generated images, which will increase the chances of detecting early, subtle disease symptoms, such as early non-proliferative diabetic retinopathy (NPDR), or optic disc changes in the evaluation of glaucoma, especially compared to current examination techniques, such as using the manual BIO examination instrument alone.

Moreover, this apparatus and system makes for the ability to share, export, send, collaboratively tag, annotate, engage in remote consultation with colleagues, or otherwise allow for viewing outside the ophthalmoscope viewfinder the images captured during or after the patient encounter within certain medical practices or academia, including viewing remotely (e.g., telemedicine). The hardware attachment (and software interaction/system) does not interfere or minimally interferes in the examination process of the patient; for example, the hardware attachment should not occlude, or minimally occlude, the view of the examiner, nor should it significantly occlude the BIO illumination source (e.g., halogen or LED light beam). In the case of a beamsplitter as part of the apparatus, the apparent brightness to the user can be lowered or raised, but not dramatically. In other aspects, the split is 70:30 (examiner:camera light intensity ratio), which in practice is clinically indistinguishable or minimally distinguishable from the traditional examination and maintains light intensity of BIO illumination well within standard illumination thresholds. In one aspect, unlike other prior art systems, the apparatus and system do not require the examiner to use a screen other than what can be seen within the scope to verify images while capturing such images.

Capturing images will be aided by multiple redundancies. In one aspect, a redundancy is automatically built in to the system; for example, if the image capture does not work as programmed, the user may still use the BIO manually as they would normally. In another aspect, if one system does not work as expected, or is inappropriate for a particular setting, an alternative method will be substituted for the same task (e.g., wireless image transfer from the device's onboard electronic storage media may not be appropriate in certain medical institutions, in which case a USB or SD card manual image transfer may be used instead or in addition to wireless transmission). Similarly, in some aspects, redundancies may include certain wireless networking technologies such as, in certain aspects, Bluetooth or one or more or variations of WiFi, as well as printing images, mobile application, web-based application, computer-based application, cloud-based application, hardware-based application, etc.

Image and video capture can be triggered by multiple methods including but not limited to via a remote app (such as on a cell phone, tablet, or computer), automatically, by a handswitch or footswitch, or by using on-device or off-device microphones and voice recognition technology conducted on-device or off-device to capture, switch imaging modes, annotate imagery, or otherwise control various elements of the device and integrated augmented examination system, without interfering with, or minimally interfering with, the usual indirect ophthalmology examination procedures conducted by the user.

In one aspect, the hardware comprises six optionally separate physical components, all of which are physically attached to a BIO instrument. Those six components comprise:

The camera attachment (in one aspect, wired to a reprogrammable microprocessor board);

Reversible mounting bracket assembly;

Optical beamsplitter attachment, optical and illumination transmission window, and optional linear plate polarizing element or elements to reduce glare;

Wired or wireless foot-pedal image trigger or other means of triggering image capture;

Embedded microprocessor, which, in one aspect, comprises a microcomputer and connected wireless antennas and sensor array integrated in the device enclosure, such as a wireless (in one embodiment, Bluetooth) connection with networked computing devices in "listening" mode awaiting input from recognized networked devices, for use cases such as, but not limited to, image review on an external networked computing device, or software-based store-and-forward image sharing; and A power source, such as an AC (alternating current) power adapter or battery, which may be connected to a wired or wireless (in one embodiment, induction coil-based) charging system or "hot-swappable" battery array system.

Regarding the camera attachment in the main device enclosure, it may exhibit exact focus correspondence (to an in-focus image manually generated by a user of the indirect ophthalmoscope using a handheld condensing lens and standard indirect ophthalmoscopy examination techniques), replicable in production to parallel rays and corresponding focal length to capture reflected rays from the beamsplitter image. In one aspect, it allows for standardized focal elements of the onboard camera, e.g., "number of turns" of the camera barrel threads, to achieve focus if using a custom camera mount. In one aspect, focus is defined by lens barrel length and should not "drift" once set; preferably, the focus ring is not accessible by the user except in a servicing situation. A variety of hardware- or software-based techniques may be used to achieve consistent focus correspondence between the aerial view of the retina through the user's handheld condensing lens, the examiner's view through the BIO instrument eyepieces, and the image captured via the onboard camera, such as a high-depth of field camera system, such as, but not limited to, the use of an onboard lens preferably with aperture greater than f4.0, unlike most embedded camera systems with narrow depth of field and aperture approximately f2.0.

In one embodiment, there is exact, or almost-exact, alignment between the camera, BIO view through the eyepieces, and device beamsplitter as enabled by precision mechanical design of the device's reversible mounting bracket mechanism, optical and illumination transmission window, and orientation of optical elements relative to the optical and illumination system enclosed wholly within the BIO instrument, which in many aspects, typically comprises a single central triangular reflecting mirror block, reflecting imagery laterally (and again, via a second set of two triangular mirror blocks) onward to the BIO instrument eyepieces; and a superiorly located illumination source reflected nearly coaxial to the optical axis of the BIO instrument via another, superior but centrally-located, angled mirror. A triangular reflecting mirror block used within a standard BIO hardware system is known to those of skill in the art. In certain cases, this may require either separate "wings" from a central hardware attachment module to accommodate secure precision alignment with different BIO instrument models, versus adjustment knobs or entirely different device enclosure models specifically form-fit to specific BIO instrument makes or models, if too large a difference exists in the mechanical design aspects between different BIO instrument models to permit consistent alignment of device elements, optical elements, and the minimal obstruction of instrument controls by use of a "universal" design of the mounting bracket mechanism.

In one embodiment, the design will use a 2-dimensional image approximating an "intermediate" image in between oculars (preferably separated by about 8 mm at external viewport, down from ~60-70 mm interpupillary distance of examiner), by a splitting ray in the middle of the viewport, central location of a partially reflective mirror positioned coaxially with the wholly-enclosed optical elements of the BIO instrument being adapted, and the central location of the device embedded camera located coaxially with the reflected image. Other embodiments may split off two image rays to two cameras, one for each viewing mirror, capturing a one-to-one 3-dimensional view, or to enable other imaging enhancements enabled by a two-camera system, such as enhanced depth of field, level of zoom, increased sharpness, expanded dynamic range, or other optical and/or sensor-based viewing enhancements of captured imagery, such as red-free fundus photography, fundus autofluorescence (FAF), or fundus angiography (FA) by the use of a second camera and specially tuned optics (such as using specialized image gratings or sensors to capture particular wavelengths of light with or without the use of intravenously-injected photo-emissive dyes such as fluorescein dye, useful in clinical examination of the fundus in conditions such as diabetic retinopathy, but traditionally requiring much larger dedicated imaging systems and dedicated technicians).

In preferred embodiments, the camera will be neither too large nor too heavy to significantly impair a typical examination, so as to maintain desirable user ergonomics during the examination session. If certain embodiments are required to be larger or heavier, the camera and mounted apparatus is designed to balance weight between front and rear sections of the camera, taking into account places where a user will touch/manipulate or where their hair or glasses could become entangled or otherwise affect the clinical examination and/or image capture. In a preferred embodiment, the apparatus taught herein will comprise an "all in one" housing design, incorporating camera, beamsplitter/optics, computing/processing/transmission/sensing means, and battery (or other power means (e.g., AC adapter)). In one embodiment, the battery may be mounted externally on the user, such as at the waist (for example on a belt), with a wired attachment to the main instrument-mounted device.

In preferred embodiments, any wires, such as the camera control wire, will not be exposed outside the apparatus, although in some embodiments the control wire and/or other wires will be exposed.

The optical system may comprise a separate, air-gapped small beamsplitter (partially-reflective mirror) to be attached or aligned over the BIO viewport. The beamsplitter, in one aspect, may be a simple 70/30 plate beamsplitter, reflecting a second ray 90° from the optical path. The beamsplitter design, rather than a coaxial camera, may be used in one aspect, having near-100% correspondence between the user's examination and the generated images with minimal requirement for the user to have to manipulate mechanical control levers on the apparatus, or to have to make significant adjustments to achieve user-camera optical correspondence before, during, or after the examination in typical use cases. The user may generate focused images (parallel rays) by, most commonly, a handheld 20-diopter or 28-diopter condensing lens as the user has been trained to do in routine indirect ophthalmoscopy, taking into account factors like image tilt, corneal distortion, and a patient's refractive error of the eye examined; when the aerial image of the ophthalmic fundus, as viewed through the handheld condensing lens, is in focus for the user, it should be in focus for the camera. The user may, in one embodiment, calibrate the device focus in a separate set-up procedure before using the instrument for the first time (in one embodiment, aided by the use of an infrared-based distance sensor) to account for the examiner's own refractive error (such as presbyopia) and allow sharp focus of the device camera upon the aerial image generated by the handheld examination lens.

In some aspects, ancillary optical systems may be used or included (e.g., condensing lenses to shrink the image, or parabolic mirrors) beyond just the camera/beamsplitter, allowing for further miniaturization and an all-in-one design, while also exhibiting technical advancements. Image distortion (e.g., using a parabolic mirror) may or may not be unacceptably introduced by such a system; in instances where a consistent type of optical distortion is produced by such additional lenses or mirrors, onboard or off-device dynamic algorithmic image processing techniques may be used to correct for or reduce distortion in the captured images. In a preferred embodiment, the optics are designed to remain securely flush and aligned with the BIO eyepiece external viewport, and not occluding or distorting (or minimally occluding or distorting) the view of the examiner, or the light from the BIO illumination source emitted through the headlamp portion of the BIO viewport and passing through the device optical transmission window.

The apparatus may be adjusted to "fit" or accommodate an array of different BIO models. Additional hardware may also be provided, such as an attachment bracket specifically designed for individual BIO makes and models, or of additional instruments, such as laser indirect ophthalmoscopes, based upon a BIO platform. The apparatus, in preferred embodiments, will incorporate a material and electrical design so as to not warp with normal use, or disallow heat dissipation by the BIO instrument's illumination source, nor damage the manual BIO instrument reversibly coupled to the device by the use of a custom-fit mounting bracket that can be, in a preferred embodiment, securely attached and detached from the BIO instrument. In aspects, the internal optical system surfaces will be matte black to reduce internal reflections/light scatter and glare (e.g., Purkinje reflections/reflexes from the cornea, tear film, patient's natural lens, and handheld condensing lens, or other stray reflections from the device and BIO instrument's internal optical system and optical/illumination transmission windows). The device, in a preferred embodiment, will allow access to the BIO instrument optical & illumination viewport and the device's own optical & illumination transmission window by simple detachment of the device from the BIO instrument for cleaning these surfaces, so as to remove dust, fingerprints, or other debris which may degrade optical performance. In another embodiment, non-corrosive coupling agents such as films or gels applied between the BIO instrument viewport and the device transmission window may or may not be used to enhance optical performance between the device herein taught and the BIO instrument adapted.

In some aspects, linear polarizers may be used to polarize light-emitting diode (LED) light and images to the camera. Software techniques and applications may also be used (e.g., frame doubling, high dynamic range [HDR] image processing algorithms), along with software image stabilization techniques to optimize light and image quality captured by the image sensor of imagery from the eye. These techniques would help optimize image quality and fidelity in settings where high-quality image capture is challenging, given the operational need to capture images with a low-enough shutter speed to capture a sharp image despite the natural movements and saccades of the patient eye being examined, the relatively dark background illumination of the examination room, the bright illumination source and numerous sources of glare during the examination, and relatively darkly-pigmented ocular structures in many patients. In certain examples often found in clinical practice, these techniques would help capture high-quality, well-exposed imagery in circumstances in which there is a large difference between dark and bright areas of the image captured, in patients with dark fundi (relatively darkly-pigmented retina and other posterior-segment structures of the eye), or in patients who are quite light-sensitive and so the illumination levels used by the BIO instrument are relatively low. Software techniques for glare reduction include, but are not limited to, eliminating imagery captured at maximum image brightness, or close to a 255 value of image brightness, when using grayscale pixel values in software image processing. To optimize image stabilization, hardware or software techniques may be used, such as automatic image stabilization computer software hosted on the device or off-device, or optical techniques such as isolation of the optical system to vibration by the use of additional elements such as, but not limited to, vibration-dampening elements surrounding the optical components such as the camera lens, image sensor, and plate beamsplitter, pivoted support elements such as gimbal stabilizers with or without onboard motors, or the use of internal springs mounted between the device external enclosure and optical platform.

Triggering the camera to capture an image may be accomplished by way of a manual or automatic handswitch, footswitch, or other networked computing device, which may be wired or wireless. In some embodiments, other aspects of the apparatus may be placed in and/or around the footswitch, such as a CPU, battery, processor, and/or other components. In a preferred embodiment, no user intervention would be required beyond the conventional techniques of indirect ophthalmoscopy; for example, auto-capture of images would occur once an in-focus retina or part(s) of the retina are detected by a combination of integrated device elements including, but not limited to, the image processor, integrated algorithmic image processing software, additional sensors such as, in one embodiment, a distometer, and device firmware. This may be computationally or algorithmically implemented. In one aspect, computer software detects whether a retina or portion of the retina is in view (e.g., based on color and/or other characteristics) and within programmed tolerance limits for distance and focus, and begins and stops capturing images automatically, either on-the-fly as high-quality fundus imagery is detected by the system by criteria such as discussed prior, or after a pre-programmed, adjustable number of images or time interval. For example, the software may stop capturing images and alert the user when an adequate capturing of the retina or portion of the retina is finished. Other criteria for starting and stopping may be used. For example, using edge detection or other image processing techniques, the software may only instruct image capture when an in-focus image is detected. Alternatively, images may be captured using a remote trigger via a computer software application ("an app") either via mobile device, web-based, or other means. By way of example, a person other than the examiner may trigger image capture on a phone, tablet, or computer, and the person may be physically located at the examiner site or in a remote location.

Upon capturing images, image export from the device onboard memory and file storage system may occur automatically, or images may be manually retrieved and exported to a separate file storage system either integral to the device, or to a removable file storage apparatus (such as, for example, SD card or a USB device). Images may also be exported wirelessly. An automatic, user-accessible file system hierarchy may, in one embodiment, attach metadata to the captured imagery and organize the images with little or no direct user intervention from the indirect ophthalmoscopy examination session. In one aspect, these images may be encrypted to protect the health information of the patient to meet HIPAA/HiTech Act requirements. For a "store and forward" image capture and review system, systems for image capture, retrieval, review, redisplay, annotation, comparison, enhancement, and storage may include directly or via a compatible software integration with, in one aspect, a software image management, electronic health record or electronic medical record (EHR/EMR) system, or document management system. Images may, in aspects, use wireless communication protocols such as Bluetooth to send to a device, such as a mobile device, or WiFi Direct transmission to individual team members or pre-authenticated hierarchical groups of authorized users (respectively here also referred to as "trusted users," or "trusted groups").

In a preferred embodiment, wireless image/data transfer is encrypted to maintain information security and/or transmitted to trusted users only. Encryption of encoded and transmitted data may be performed on-device or off-device, and in a preferred embodiment, network security will be maintained across all associated networked access points and connected devices. In aspects, this wireless data transfer will occur via local retransmission using accepted wireless data transmission standards (such as, but not limited to, WiFi and Bluetooth connections) to a mobile device, web app, or computer, such as between teacher(s) and student(s). In a preferred embodiment, radio frequencies and transmission standards used for wireless communication between connected devices and the transmitting device antenna array will balance goals of low-power connections, ease and stability of connectivity, data transmission speeds, line-of-sight requirements, distance of data transmission required, number of wireless connections required per device, and accepted standards and preferred radio frequencies for medical wireless data transmission to minimize electromagnetic interference with other technologies used in the medical environment. In a preferred embodiment, one-time auto-pairing between trusted user and device will happen; otherwise, sharing/pairing is set once each time the user is changed.

Regarding the microprocessor aspect of the apparatus, such as a computer processing unit ("CPU"), in one embodiment, the system used by the camera and apparatus could be a microprocessor. Another option is to use a pre-processing chip on the camera, which are, for example, used in certain webcams, which might conduct the majority of the processing either on a mobile phone, tablet, or computer, or in the handswitch or footswitch. In a preferred embodiment, a system on chip (SoC) or system on module (SOM) design platform will be used; advantages include but are not limited to reduced size, reduced cost, and easier and enhanced maintenance capabilities of the platform. In preferred embodiments, small, lightweight processors will be used to enable processing, and in one aspect, an all-in-one single board computer system could be used. A cross-compiling toolchain may also be used. Integrated software applications hosted on remote networked computing devices may also act as remote controllers of the device, such as, but not limited to, a web-based app or an app on a mobile device or computer.

The use of onboard microprocessor, integrated image processing computational elements, wireless networking capabilities, and integrated device firmware and supported software applications together enable several other advantages beyond the prior art. Examples of these advantages include, but are not limited to, on-the-fly switching between one or more wirelessly-connected remote displays concurrent, or subsequent to, the clinical examination session, without interruption of the image capture, device operation during indirect ophthalmoscopy, or video stream generated by the device and user in a particular examination session. Additionally, integrating authentication of clinical users with a particular device, location, and examination session, may enable clinical collaboration significantly beyond the prior art. In one embodiment, the use of authenticated device users, wireless image and video capture and transmission, wireless bidirectional data transfer, onboard programmable microprocessor, remote redisplay of imagery generated in a clinical examination session, and compatible integrated off-device software applications can enable concurrent or time-delayed communications between clinical colleagues either in close or remote physical proximity via a separate clinical software application. Bidirectional wireless data transfer can enable, in one aspect, remotely-triggered image capture, remote switching of device modes, or remotely enabling other device functions without the user's need for direct intervention. Examples of these advantages include, but are not limited to, the eye physician user checking image quality of the capture session after capturing imagery from one eye on their connected smartphone; annotating the imagery with certain notes and flagging the image for review by a senior physician and sending a quiz question based upon the imagery to a junior colleague via the software application user interface; a junior resident physician simultaneously viewing the examination session imagery via their own connected mobile device to learn the techniques of indirect ophthalmoscopy and for vitreoretinal medical education purposes; one or more remotely-located physicians observing the imaging session concurrently with the examination or in a time-delayed fashion, making clinical observations into the communications interface in compatible Internet software applications during a Grand Rounds medical educations conference; and a senior physician verifying the quality and completeness of the indirect ophthalmoscopy examination, switching image capture modes at a certain point from a nearby networked computing device in order to better capture a desired ocular feature while signaling the mode shift to the user using audio and haptic cues, all without an interruption in the medical examination process.

In one preferred embodiment, the embedded microprocessor and wireless antenna array, along with integrated, secure remote networking software such as virtual private network (VPN) software, along with algorithmic techniques such as packet forwarding, will allow pre-authenticated, authorized ("trusted") system technicians to troubleshoot, maintain, and update the device or groups of devices and integrated system remotely and provide automatic periodic updates to enhance system stability, security, and enable automatic rollout of new software-enabled functions and enhanced functionality of the BIO digital adapter system over time. This provides additional substantial advantages to the prior art, as substantial improvements in device functionality and reliability can be made remotely and wirelessly over time to one or more devices or designated groups of devices via software or firmware updates to the reprogrammable device microprocessor, and in one aspect, device error messages or the need for system maintenance can be wirelessly sent to compatible networked devices or off-device networked software application interfaces to signal system administrators that maintenance functions are necessary for a particular device (which, via location-based tracking as described prior, can help the system administrator pinpoint a specific device location and particular doctors who may need replacement devices). In a particularly large multi-specialty practice or hospital-based setting, these sorts of remote device administration features enabled by the device taught here offer substantial advantages beyond tedious periodic inspection of each device within a practice for already-busy practice personnel and ancillary staff members.

The microprocessor and integrated on-device image processing, device firmware, and integrated off-device networked software applications, in one aspect, will allow for auto-montage of the retina and ocular fundus. Auto-montage can be described as the automatic, or software-assisted, joining, through one or more established or novel algorithmic techniques, of adjacent ocular fundus imagery captured through individual overlapping images or sets of images through the relatively narrow field of view of the handheld condensing lens used in indirect ophthalmoscopy, relative to the full span of the ocular fundus as viewed by the complete examination of each eye. The fundus montage would offer a full "map" of the fundus of each eye in a single high-resolution image; have, in one aspect, the ability to compensate for distorted or incomplete capture of features in one or more individual image captures; provide an easily-magnified image that could be stored, retrieved, and compared to prior examination montage images; and provide a "global" view of the fundus as a whole, as opposed to the narrow "keyhole" view of individual images viewed under high magnification through the handheld lens. The montage would typically be examined on an off-device display by the user or third-party reviewer at the end of the examination, or at the beginning of a follow-up examination to, for example, compare patient's examinations for progression versus stability of any clinical pathology found. In one aspect, a process would "stitch together" more than one image of the retina or ocular fundus (here shortened to simply "the fundus"), or of other ocular features, to provide a more complete picture of a larger portion of the retina or ocular fundus than just one picture of one portion of the retina or fundus, allowing for quick review of the entire fundus at one time, rather than scanning through a library of images of successive portions of the fundus. Several existing technologies, essentially image stitching algorithms, may assist with the auto-montage feature, in addition to or beyond any novel techniques used. These existing technologies will be familiar to one of ordinary skill in the art. On-device or post-processing enhancements may be assisted by the use of embedded sensors on or enclosed in the device and connected peripheral elements such as accelerometers, infrared-based distance sensors, or gyroscopes, to automatically detect or suggest image orientation, portion of the fundus examined in an image frame, etc.

A sensor array may be provided on the imaging device disclosed herein including one or more of the sensors as described directly above or elsewhere in the application.

The processor or other software may also allow for auto-crop and auto-center with a black frame typical of standard fundus photographs. Auto-crop may be described as the automatic, algorithmic removal of extraneous imagery captured by the onboard system beyond the ocular features desired to be captured, which may or may not be used in combination with the algorithmic placement of a standardized black frame with or without standard orientation marks as typically seen in high-quality fundus photographs. Auto-center may be described as the automatic, algorithmic recognition of the circular handheld condensing lens ring held by the examiner and centration of this ring in the captured fundus photograph, with or without additional image processing techniques such as adjustment for tilt of the lens (forming an ellipse, rather than a circle in the captured photograph) to minimize distortions in the captured photograph where applicable. The images produced by these techniques allow for easy comparison of fundus photos generated by the system described herein to traditional fundus photographs that examiners typically inspect as generated by currently existing fundus photography technology. The onboard device image processor or other post-processing software may also reduce/eliminate ambient lighting artifacts (such as, by way of an example, fluorescent lighting). The processing or other post-processing software may include providing a red-free image or reduced-red image to better distinguish between blood, vessels, and the ordinarily orange or reddish features of the ocular fundus. The use of a reprogrammable, wirelessly networked device microprocessor and integrated software applications hosted on- or off-device allows a variety of options to exist to correct for imagery captured in a flipped or reversed orientation beyond the prior art, which largely must rely on optical elements to correctly orient the imagery captured, or subsequent manual manipulation of captured images on separate computer software requiring substantial user intervention. In a preferred embodiment, correction of image or video orientation may be performed in real time or near real time to the clinical examination by on video processing of the camera output, which represents a standard improvement versus direct mirror of video output. Furthermore, ophthalmic imagery captured may be in real time or near real time re-oriented by such software- and hardware-based techniques in the taught system to their correct anatomic orientation (which is ordinarily reversed and flipped in the aerial image as viewed through the handheld condensing lens used in indirect ophthalmoscopy).

A variety of data science, image processing, and computer science algorithmic techniques may be employed to further enhance the diagnostic and medical record-keeping capabilities of the integrated system here taught. Algorithmic techniques such as, but not limited to, machine learning-based automated image element recognition for the system may also be included as part of the device and system. Such technology may be used to, for example, recognize that a focused retina is in view (to initiate capture), to recognize which eye is examined, and when a higher level of image magnification is used or needed (for example, to capture a high-quality image of the optic nerve head of each eye), to locate large library/libraries of tagged fundus images (e.g., right or left) for algorithmic computer vision-based fundus photography image grading using computing applications and algorithms such as, but not limited to, TensorFlow, and/or rapidly collect large datasets of clinical imagery alone or in combination with clinical metadata for artificial intelligence-based healthcare automation software systems such as, to name one example, DeepMind Health. In one embodiment, optimized software libraries for machine learning can be integrated with the device microprocessor or image coprocessor to enable rapid acquisition of algorithmically enhanced or recognized imagery, balancing the power and data storage limitations of the portable embedded system taught herein. Bidirectional data transfer and device control capabilities of the embedded system taught herein can also, in one embodiment, use recognized user and patient states based upon algorithmically-recognized ocular features to enable or simplify automatic or manual switching between disparate imaging modes optimized for high-quality capture of various desired structures imaged in and around the eye of the patient under examination.

The battery and integrated device power management system, in a preferred embodiment, will feature a distinction between low-power and high-power states (also here referred to "sleep/wake" states), to switch from sleep to wake states when the user needs to use the apparatus. For example, in one embodiment, the device will "wake" whenever a user picks up the BIO instrument from the wall by use of onboard sensors such as an accelerometer, thereby not requiring manually powering on the device by the use of a physical switch each time a user puts a BIO on his/her head. In some embodiments, the device may be charged by an AC adapter. In some embodiments the device will include a battery to support fully untethered use of the device. The battery may be an integrated rechargeable battery, or also could, in one embodiment, support a "hot swappable" array of user-replaceable batteries to extend use time over an extended clinical session; in one aspect, the battery may be recharged by a universal serial bus (USB) charging cable and compatible alternating current (AC) adapter or separate power storage system. In another aspect, the device will be charged when placed into a dedicated charging station or holding base. In another aspect, the device may be charged from the BIO charging cradle either directly, by the use of a coupled charging adapter custom-fit to each model of charging cradle, such as those commonly used to charge "wireless" BIO instrument models (commonly described as "wireless," in that they use onboard rechargeable batteries, versus a wired AC power connection). In another embodiment, charging of the device could be conducted using an adjacent wired or wireless charging station (using, in one embodiment, wireless battery charging technologies such as wireless induction coil-based charging), enabling the quick use and replacement of the device throughout a busy clinical workflow and the simple continued recharging of the device in between patient examination sessions.

Data formats for device capture, manipulation, storage, retrieval, and transmission of data that is created and stored by the device are referred to as, in some aspects, documents. A document may contain multiple blocks of data received from the hardware device. These blocks of data are referred to as pages. A document must contain at least 1 page, but has no upper limit on the number of pages. An exception to this is if there are errors on the device. In that case, a document with no pages can be returned, but the error collection will be filled in. Also, if there are errors, the document may still contain pages. However, these pages should be assumed to represent invalid data. Documents are grouped together in a session, which generally represents a patient exam. Sessions may contain documents obtained from multiple different hardware devices. Each session, document, and page within the documents may have searchable metadata that is not patient identifiable. This is to provide a quick means of searching the data captured and stored without having to decrypt every record.

In one aspect, the basic structure may appear as follows. A session may comprise, but is not limited to: globally unique ID; MRN, which in preferred embodiments is either an encrypted value, or a hash of a value that is stored elsewhere; Name; Description; Start Timestamp; End Timestamp; Responsible User IDs; Documents; and Device Groups associated with the Session.

A Document may comprise, but is not limited to: globally unique ID; Device ID; Operator ID; Pages; Metadata entries; and Messages. Documents will contain at least one Page or Message.

A Page may comprise, but is not limited to: globally unique ID; Data. Type Description; Data Format; Filename; DataURI (Data Uniform Resource Identifier), in a preferred embodiment the raw data is stored in a different data source to keep actual patient data isolated from identifying data; Timestamp; Metadata entries.

A Metadata entry may comprise, but not limited to: globally unique ID; Key; and Value.

A Message may comprise, but is not limited to: globally unique ID; Device ID; Device Message ID; Message Severity; Message Type; Text; and Timestamp.

A Device Group may comprise, but is not limited to: globally unique ID; Name; Description; Session ID; and Devices.

A Device may comprise, but is not limited to: globally unique ID; Name; Description; DeviceType; and Device Group ID.

A DeviceType may comprise, but is not limited to: ID and Name.

In other embodiments, different file formats may encode other types of metadata. Different devices or device versions may encode, in certain embodiments, the state of the software configuration, the state of the device, and calibration data, that excludes patient-specific or protected health information. In certain embodiments, these may include an IP address of the device, the software and hardware version of the device, the device geolocation of the device, or other device- or user-specific data useful to device management and interpretation of the data but not specific to the patient-related data itself.

In embodiments, the above data format may be used for:

Sessions

Sessions, in embodiments, may be analogous to patient visits. There will typically be a one-to-one correspondence between a session and a patient visit. In aspects, sessions are not connection instances since a web service may be used; accordingly, connections may not necessarily be held open. Sessions can be created, started, stopped, etc. via a website, for example. This allows the workflow of associating device documents with a session that is not associated with an MRN, and then allowing a user to manually split that data into sessions linked to MRNs. For example, a user could use the timestamps of the documents.

Documents

Documents may comprise, in aspects, a single "upload" of data from a Device to a Session. In aspects, a Document will be one Page; for example, a fundus image. In other aspects, a Document will comprise multiple pages, allowing for, for example, a burst of images from the device and uploading the images in one step, saving different file formats, saving other types of data along with the data (e.g., audio, left and right eye images, etc.). In one embodiment, a Document may be sent from a device to a Session that contains only a Message. Messages, in one aspect, comprise a data type well-suited for device status-related information such as, for example, "Battery Level," as they include, in aspects, Acuity and Message Type. In this example, if the device onboard battery is at 20% charge, the user may receive a Warning Message, but at 5% charge, the user could, in this embodiment, receive a Critical Message. In this embodiment, as the device detects a low battery charge, the system may send a device status-related message without being restricted by whether the user captures an image.

Pages

Pages, in aspects, comprise raw data from the Device, along with data format info for storage information.

Metadata

Metadata, in aspects, is used to store "out of band" data that may be useful to the user. This may include, but is not limited to, calibration data, software/hardware versions, geolocation data, etc.

Devices

Device records, in aspects, may comprise data for the user and the server to identify a device that is registered with the system.

Device Groups

Device Groups, in aspects, comprise collections of Devices that can be associated with a Session. For example, this may be used to set up all Devices in a particular examination room to be grouped in a Device Group. When a user creates a Session for a patient, the information may key, for example: "Patient will be in Examination Room B; associate Examination Room B Device Group with the Session." Accordingly, all devices in Examination Room B are automatically linked to the Session and will send accompanying Documents to the correct data location. Device Groups, in aspects, may contain a single device if it is desired that devices not be grouped together.

The system taught herein may also be used as part of or in electronic (wired or wireless) bidirectional connection with a paired data management control device (here referred to as a "hub") to manage and organize devices, examinations, and people involved in the examination process and associated data produced by each correctly and across the clinical data network. The hub comprises a processor (e.g., a CPU) and may be connected to the Internet with wire(s) or wirelessly. It may also be unconnected from the Internet in a dedicated local area network (LAN) or wide area network (WAN). In a preferred embodiment, the hub will be wirelessly connected to devices or examiners in the examining facility to monitor activity and permit multiple device control and coordination. In one aspect, the hub will receive images and data/information from the device taught herein or other devices. It will be used, along with uniquely identifiable markers such as hardware tokens, paired mobile devices, or passcodes, to detect and manage the hierarchy of trusted users engaged in use of a connected network of devices as previously described. It will break down the data, review the data, analyze the data, manage for storage, sync images and information, process images or information, and/or manage remote data synchronization and/or local or remote redisplay. It may also manage storing such information locally or remotely.

For example, the hub may be connected to several devices taught herein within a facility. The hub will record when such devices are being used and who is using the devices to automatically, or with minimal user intervention, maintain a secure hierarchical audit trail of clinical data generated by the clinical data network here described. The hub will log, save, organize, and process such information in order to, among other things, know when examinations were being performed, what kind of examinations were being performed, and who was performing such examinations. Personnel in or around the facility may be tracked, in one aspect, by having a radio-frequency identification (RFID)- or near field communications (NFC)-compatible tracking device on their person, or by tracking a paired mobile phone or some other electronic device wirelessly by a variety of hardware-assisted and algorithmic software methods such as, but not limited to, location-based and time of flight-based wireless tracking. The information collected by the hub may be cross-referenced with other information, for example a reference clinical schedule, to track activity in or around the facility. In another example, the hub may automatically, or with user input, pair patient imagery and metadata collected during an examination with the specific patient and associated doctor at that appointment time, with the hub subsequently associating and exporting collected data to the patient's EMR/EHR based on the reference clinical schedule used.

Figure 2:
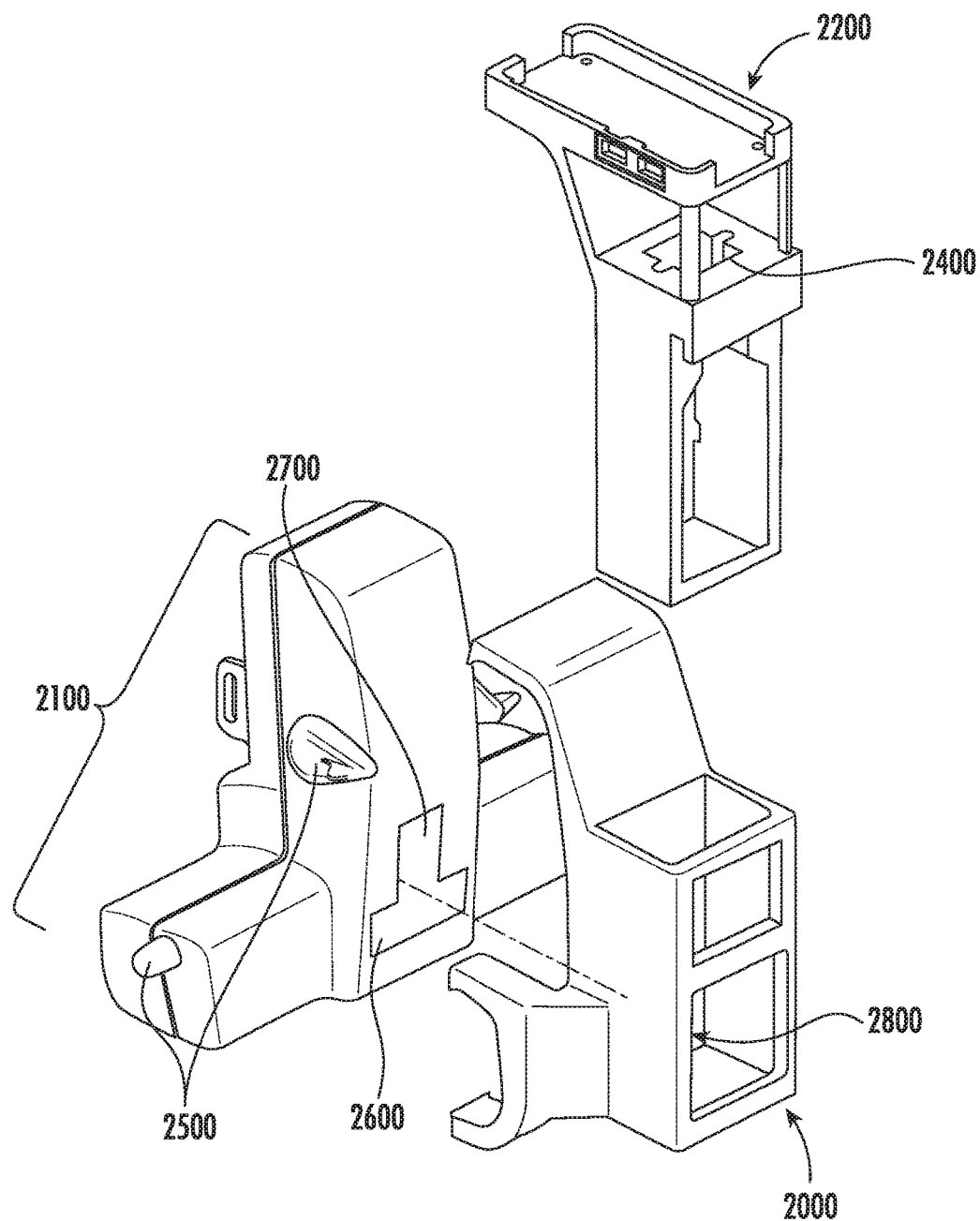
FIG. 2 is a schematic diagram of a depiction of one possible embodiment of the device taught herein, including the BIO, mounting bracket, and optional optical cartridge, with certain components disconnected and shown separately. The cartridge is optional as a separate or separable component. The mounting bracket and cartridge can all be one piece, such as a singular or modular molded, formed, casted, constructed, extruded, pultruded, shaped, connected, united, associated, coupled, joined, affixed, linked, bonded, fastened, appended, glued, attached, or 3-D printed piece.

Now turning to the Figures, FIG. 1 shows a computer-generated image of the device as an assembled enclosure apparatus (e.g., optics, camera, and electronic elements (not shown, for clarity)), including the BIO 1100, reversible mounting bracket 1000, and optical cartridge 1200, which optionally fits into or on the mounting bracket). FIG. 2 shows a three-quarters exploded view of the optical cartridge 2200, mounting bracket 2000, and sample BIO 2100 of FIG. 1 split into three separate components, with dashed lines indicating alignment of the respective elements for assembly, in this particular embodiment. Regarding the BIO and its viewport, this component may vary depending on the make/model of the BIO instrument and the device taught herein will allow for different mounting brackets to fit the varying types of BIOs and/or BIO viewpieces/viewports, by manufacturer. Optionally, the bracket may be adjusted to fit different viewpieces with, for example, sliding pieces, snap-in-place mounting elements, adjustable knobs, or other means of adjusting the bracket so it can be adjusted to optimally fit different types of BIO view ports/BIO viewpieces/BIOs without requiring disassembly, modification, or damage to the BIO instrument being adapted.

The cartridge 1200, 2200 is optional. The optics and other components may be on the mounting bracket or otherwise incorporated into or onto the mounting bracket and not necessarily incorporated by a removable cartridge. In one embodiment, the cartridge is incorporated as part of a single unit including the mounting bracket and all optical and electrical components, which in an embodiment, is a single molded piece (or interlocking piece) incorporating the elements of the imaging device taught herein. The optional cartridge, if the embodiment includes a cartridge, may be removably attached to the mounting bracket or BIO 1100 using one or more of the following:

a. a bracket mechanism,
   b. a sliding mechanism,
   c. a clip mechanism,
   d. an expansion joint mechanism,
   e. tension spring(s),
   f. magnets(s),
   g. fastening tab(s),
   h. interlocking component assembly,
   i. molded-fit assembly,
   j. press-on assembly,
   k. hook-and-eyelet,
   l. snap fastener(s),
   m. snap-fit joint(s),
   n. removable adhesive,
   o. interlocking joint(s),
   p. snap-on joining mechanism,
   q. cantilever joining mechanism,
   r. U-shaped, torsional, and/or annular snap-fit joining assembly techniques, and/or
   s. mechanisms in which a protruding part of one component is deflected during a joining operation and catches in a depression in a mating component.

Full or partial adjustment of BIO controls is permitted by the device's mounting bracket and device enclosure design elements (such as, for example, levers/knobs (e.g., 1500 in FIG. 1) through specially-designed mounting bracket cutouts, and other means for adjusting the device to fit different BIOs and BIO view pieces/viewports).

The optical cartridge 1200, in the pictured embodiment, fits into or on the mounting bracket 1000. A beamsplitter may fit into a slot 1300 in the optical cartridge. As pictured, for example, a beamsplitter glass fits into the pictured slot at a 45-degree angle to the incident ray and the beamsplitter generally fits into that area of the cartridge. In one aspect, above the area for the beam splitter, a fitting or slot for the camera is situated 1400, in which a camera (e.g., optics, lens, image capturing means, electronics, and focusing/adjusting mechanism) may be placed and secured into desired optical alignment with the BIO viewport, its internal optical and illumination system, and the view through the BIO instrument eyepieces. The view is centrally coaxial and identical with the examiner's view. On the top of the cartridge, as pictured, an area exists for additional components, although components may be located elsewhere on the device or not on the device. Such components include, but are not limited to, a battery charger, an accelerometer, a wireless or wired charging means or connection, a WiFi or Bluetooth chip (wireless network chip), a battery, a microprocessor, an antenna(s), a microphone, a speaker, a power controller, switches (for example, for on/off or other commands), and status LED(s) (for example, for indicating on/off, error, ready for certain commands, etc.). The status LEDs will be designed, in a preferred embodiment, to be viewed at a distance, while remaining unobtrusive during the eye examination in a darkened examination room, while the BIO instrument and attached device is positioned in its wall-mounted battery charging cradle.

In one embodiment, a microprocessor, antenna(s), and power supply is positioned as a unit into the top of the optional optical cartridge, the camera assembly is positioned as a unit into the corresponding cavity in the middle section below the support risers, and the beamsplitter and optical and illumination transmission window or cutouts for BIO illumination source and viewport are in the bottom section. In one embodiment, the pictured apparatus slides into place as one section like a cartridge into a mounting bracket adapter and, in an embodiment, there will exist different modular mounting brackets to fit different BIO instrument models.

FIG. 2 shows another embodiment of the device. The mounting bracket 2000 with optional cartridge 2200 is shown (along with the area or slot for a camera 2400). The BIO is shown as 2100 with BIO adjustment levers or knobs 2500. In this depiction, the BIO front viewport or front viewing window is shown 2600. Also, the BIO illumination window is shown 2700. Finally, the mounting bracket transmission window is depicted 2800.

Figure 3:
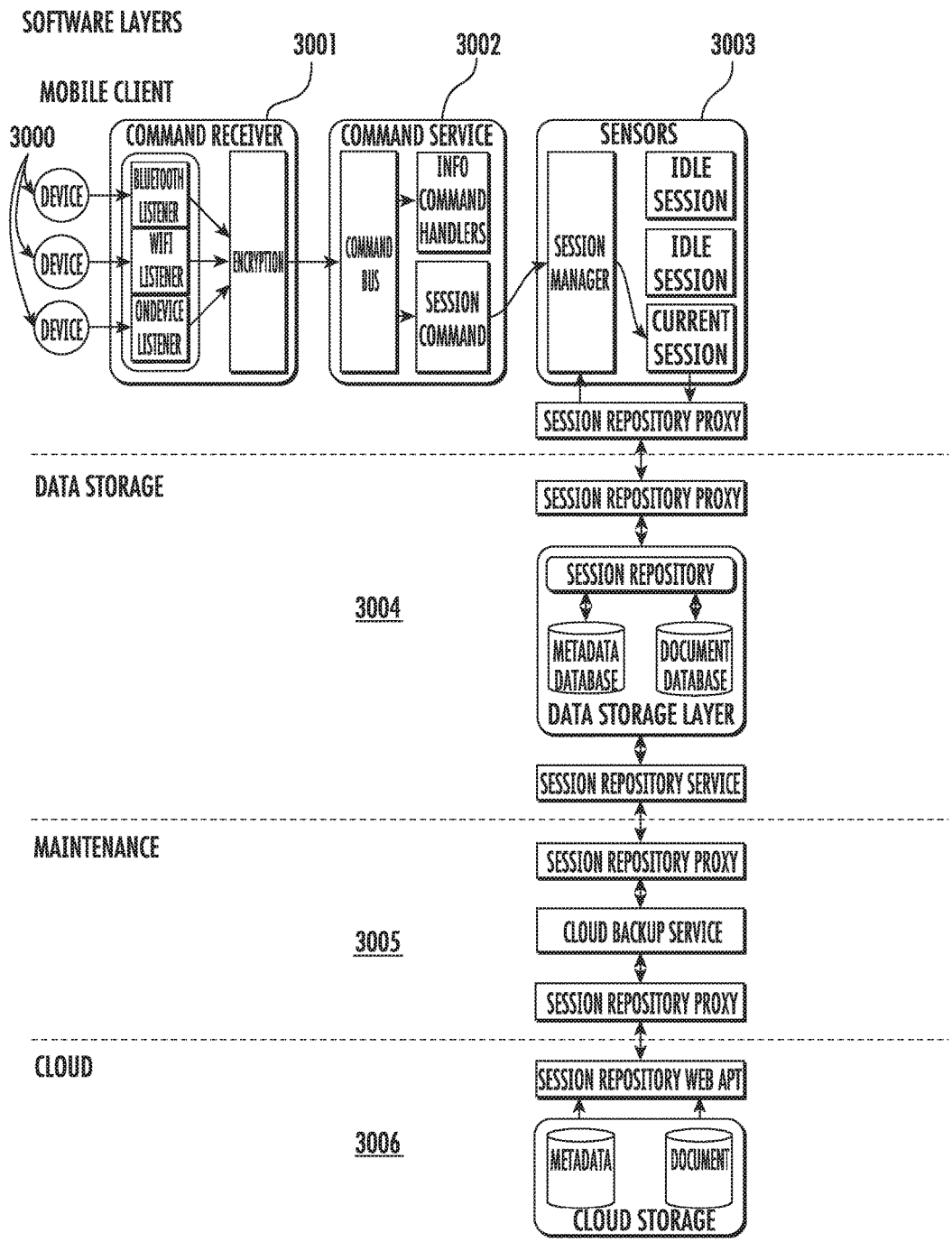
FIG. 3. is a flowchart showing possible software layers used to share and store captured and processed images.

FIG. 3 shows a flowchart of the high-level architecture of the system software application(s) used to implement the intended purpose of the imaging device taught herein. Specifically, a block diagram is shown depicting data transmission and conceptual hierarchy or software layers and services. In one embodiment, at the command receiver level, the image captured by the device(s) 3000 will be sent by Bluetooth, WiFi, by wire, or by OnDevice listeners. The data may be encrypted 3001. Next, the command service function is performed, wherein a command bus handles info command and session command 3002. Clinical data capture sessions are then managed and if there is a current session, information flows to the session repository proxy 3003 and then to the data storage layer 3004 and information such as documents, information, images, and/or metadata are stored in a session repository before moving to maintenance 3005. At the maintenance level, the documents, information, images, and/or metadata are backed up to cloud-based storage 3006.

Figure 4:
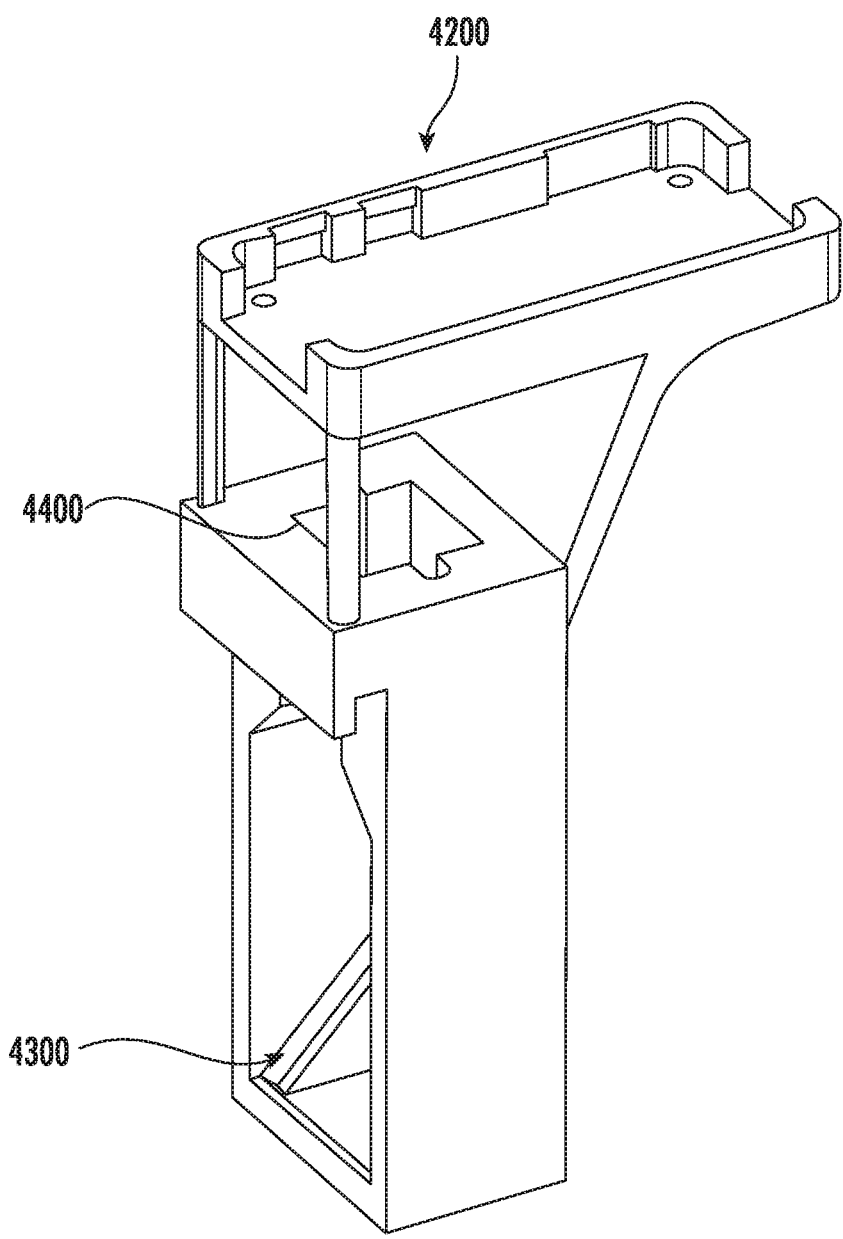
FIG. 4 is a schematic diagram of a depiction of one possible embodiment of the device taught herein, specifically the optionally separable optical cartridge.

FIG. 4 is a three-quarters view close up of another embodiment of the central optional optical cartridge 4200 described herein, without optics and electronic elements. In the bottom opening, the slot for the beam splitter glass is shown 4300. In one aspect, 30% of the light (image) gets bounced 90° up to the miniaturized camera, and 70% passes straight on to the viewport of the BIO unobstructed. The camera location or slot for the on-board camera is shown at 4400.

Figure 5:
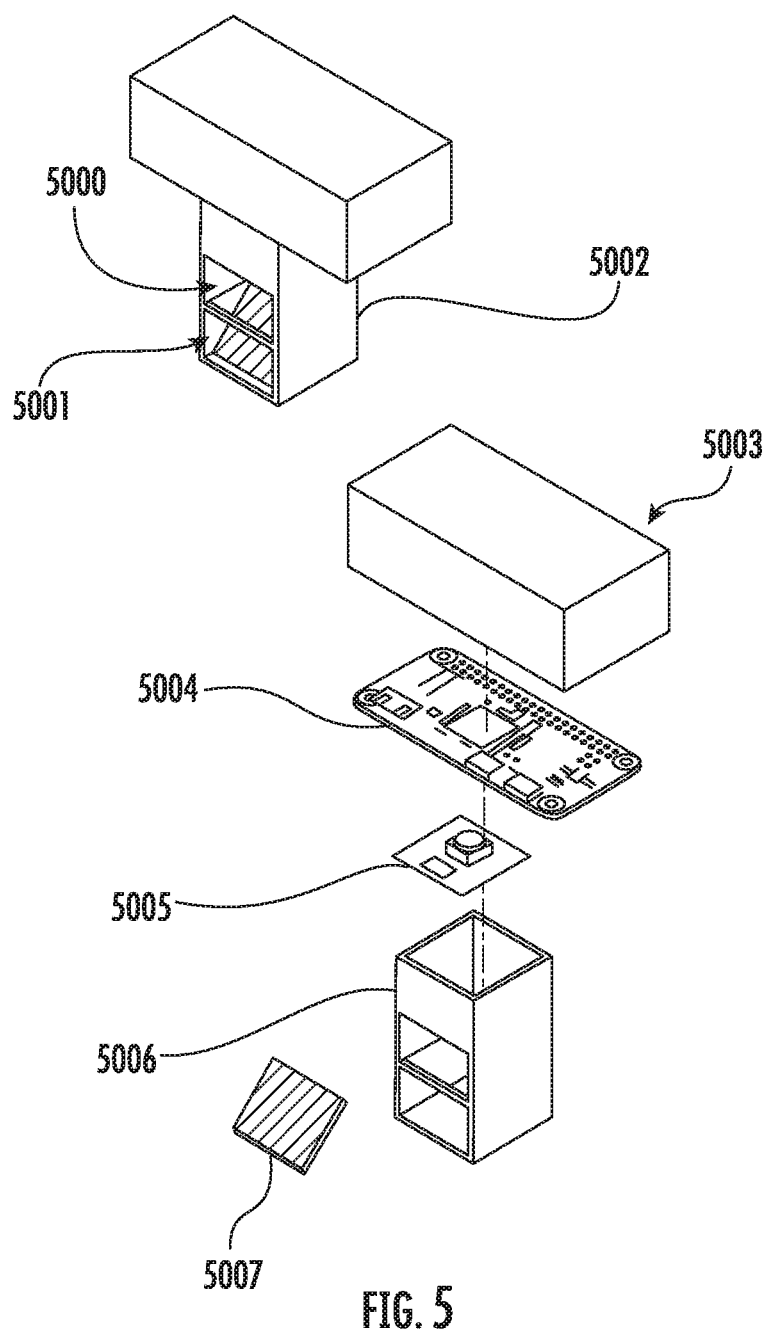
FIG. 5 is a schematic diagram of a depiction of one possible embodiment of the device taught herein.

FIG. 5 shows an exploded view of major components of assembly of the apparatus taught herein, including depictions of the apparatus assembled and disassembled into separate parts. As depicted, an illumination transmission window 5000 allowing passage of light from the BIO illumination source is shown along with an optical transmission window 5001 through which incident light from the eye passes to the BIO viewport and to the examiner. On the other side, a viewing window 5002 allows for transmission of light to the BIO viewport and then to the examiner. A computer module housing is shown at 5003 to which, for example, a single or multiple board computer, or system on module, 5004 is associated. The one or more camera is shown in 5005. And an optical housing 5006 for the camera and beamsplitter 5007 is shown which aligns the camera elements above and coaxial with the reflected image of the eye under examination. The housing also provides space for the converging optical elements, such as the incident light, on-board camera, beamsplitter, and outgoing illumination beam, and is coated with a matte black finish, in a preferred embodiment, to reduce glare from stray or unwanted reflected light sources.

Figure 6:
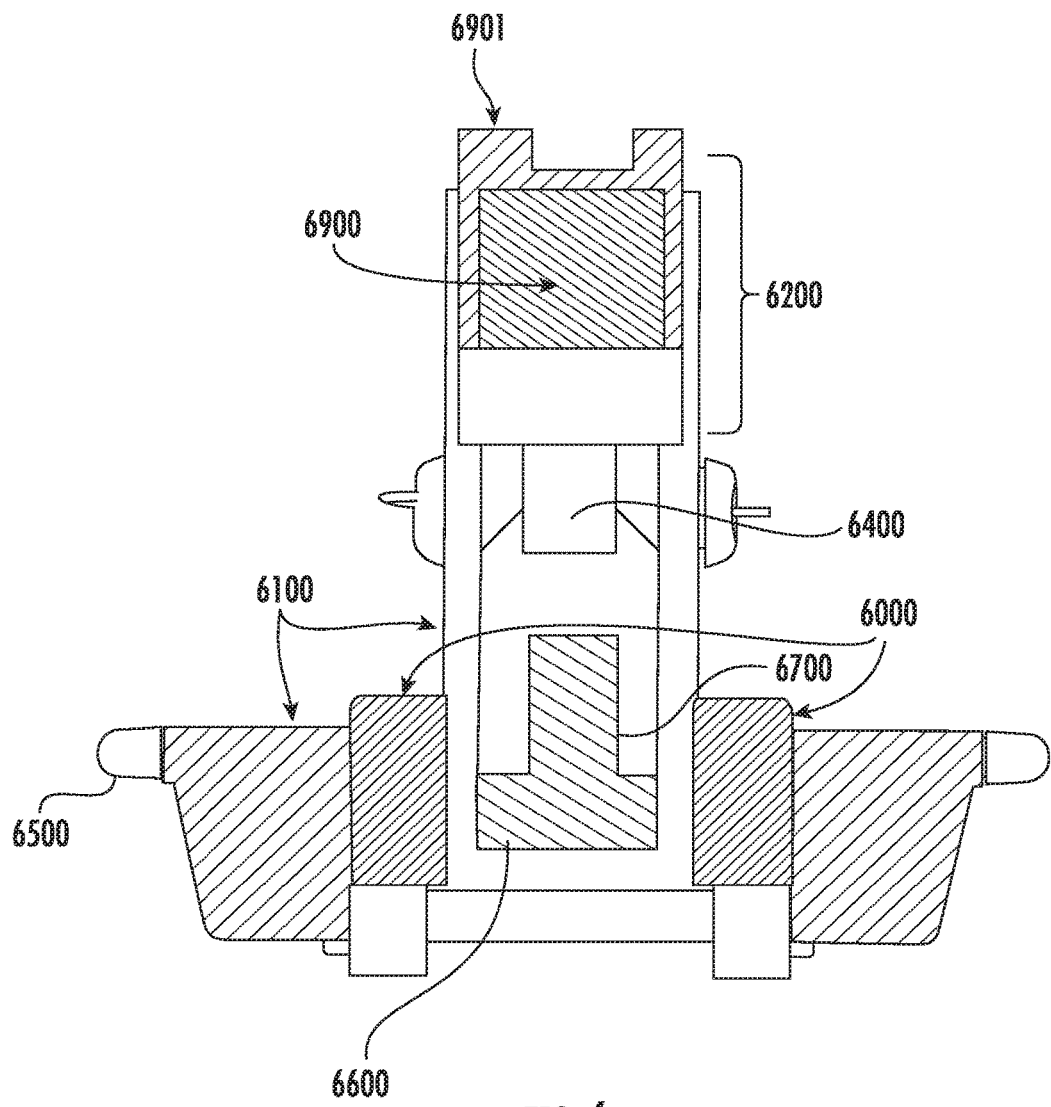
FIG. 6 is a schematic diagram of a depiction of one possible embodiment of the device taught herein, including the BIO, mounting bracket, and optional optical cartridge.

FIG. 6. shows a front-facing view of the BIO augmented imaging adapter assembly, including a BIO 6100, a BIO viewport 6600 with optional polarization (e.g., linear polarization) of light to minimize glare, a BIO illumination window 6700 with optional polarization (e.g., linear polarization) of light to minimize glare, a front-mounted mounting bracket 6000, optical assembly (optionally an attached and/or removable cartridge) 6200, camera 6400, microprocessor 6900, and antenna/battery/sensor array configuration 6901. The existing BIO mounting adjustment knobs 6500 are fully accessible due to custom mounting bracket design with device-specific cutouts for adjustment mechanisms, even with the inventive device explained herein attached and functional. The microprocessor, wireless antenna, battery, sensor array housed in the optional optical cartridge allow for image/video transmission and/or processing, system control via multiple mechanisms (mechanical, voice, mobile application, local or remote computer control, handheld or footswitch-type remote controller), and bidirectional data transmission and telemetry.

The device allows for full or almost full transmission of the existing BIO illumination source, but may also include additional sources of illumination, and an optional polarization of light to minimize glare.

Figure 7:
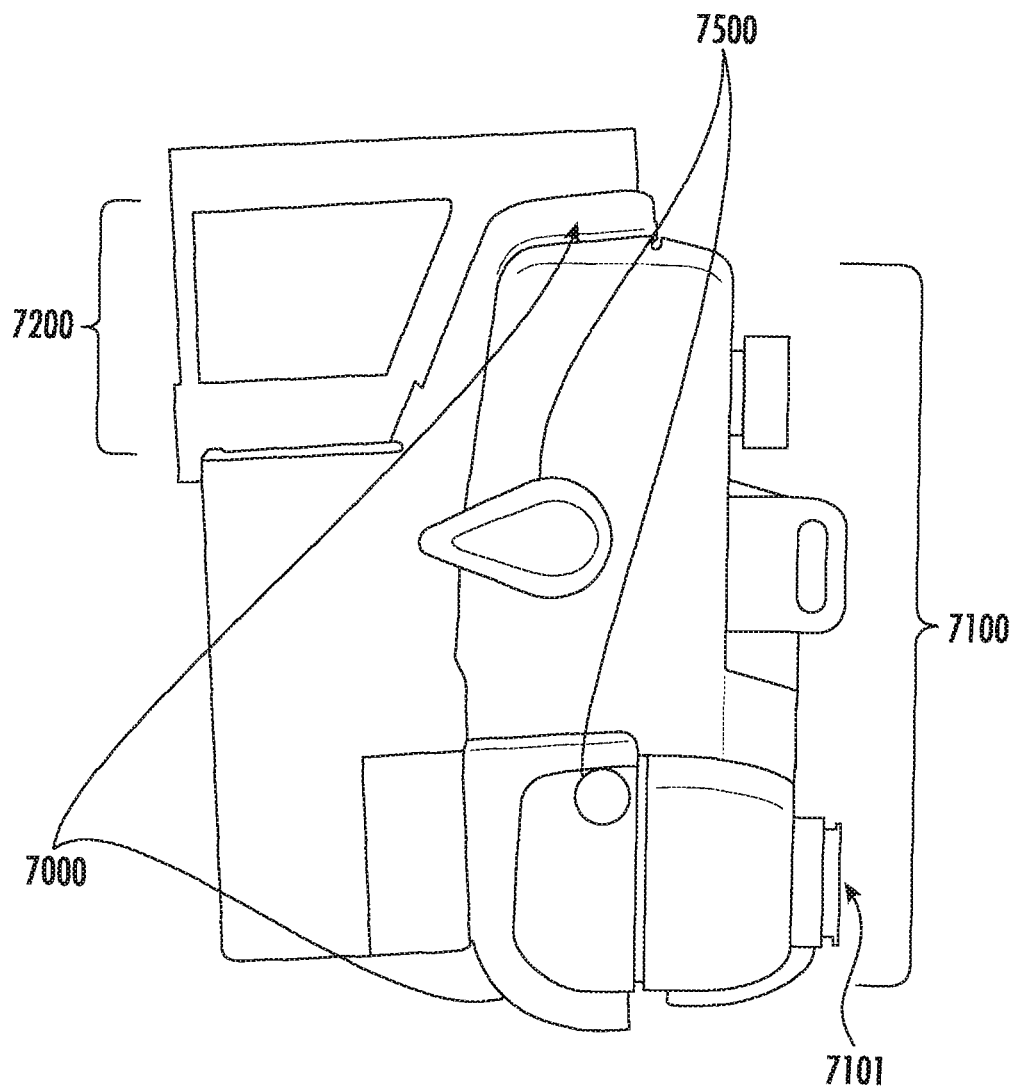
FIG. 7 is a schematic diagram of a depiction of one possible embodiment of the device taught herein, including the BIO, mounting bracket, and optional optical cartridge.

FIG. 7 is a side-view of the BIO augmented imaging adapter assembly, including the BIO 7100, front-mounted bracket assembly 7000, optical assembly 7200, camera, and microprocessor/antenna/battery/sensor array. Knobs and levers 7500 on the existing BIO device are unobstructed by the mounting adapter design in preferred embodiments, allowing for full functionality of the BIO device as familiar by examiners. The mounting bracket allows for flush mounting against the BIO viewpiece for precise image alignment of the camera with the examiner's view. The BIO viewing eyepiece 7101 as adapted to by the device taught herein allows for unobstructed, direct view from multiple models of BIO instruments to the embedded camera system. The mounting bracket may be adjustable to account for different makes/models of BIO instruments, or it may be custom-designed to fit particular makes/models. The BIO viewing eyepiece along with the imaging device design allows for unobstructed, direct view by an examiner and coaxial redisplay of the view from multiple models of BIO instruments to the embedded camera system.

Figure 8:
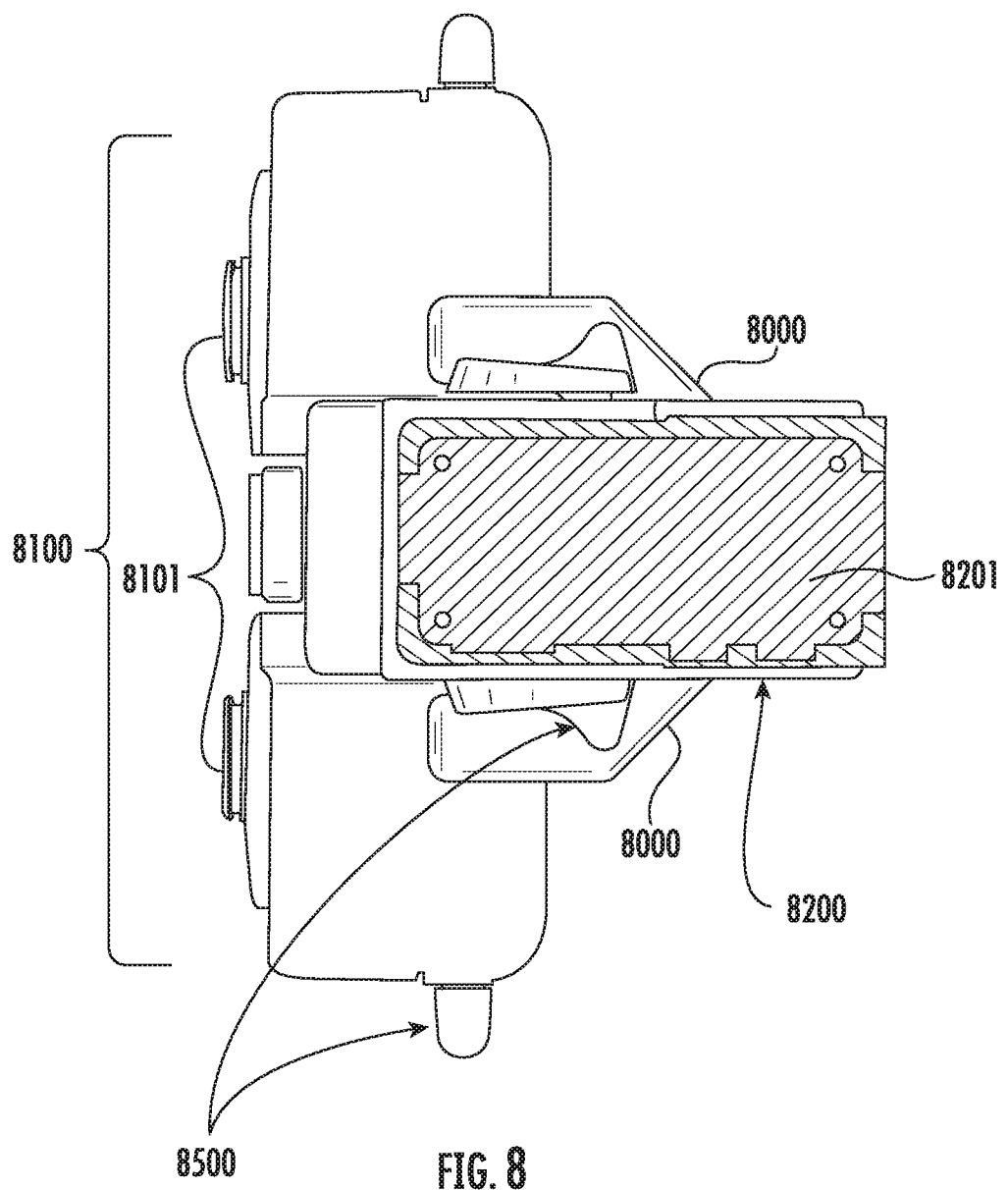
FIG. 8 is a schematic diagram of a depiction of one possible embodiment of the device taught herein, including the BIO, mounting bracket, and optional optical cartridge.

In FIG. 8. is a top-down view of the BIO augmented imaging adapter assembly, including the BIO 8100, front-mounted bracket 8000, and optionally removable optical cartridge 8200. In embodiments, the low-profile, interchangeable mounting bracket assembly allows for stable, precise optical alignment and capture of examination imagery and sensor data, without impeding the view, interfering with clinical examination, or impeding ergonomics. The enclosure on the optical cartridge for the microprocessor and other components, such as the camera, and microprocessor/antenna/battery/sensor array, is prominently featured 8201. In preferred embodiments, towards the top of the optical cartridge is where the components will be enclosed. In a preferred embodiment, the BIO instrument eyepieces 8101 have an interpupillary distance adjustment mechanism(s), which remains fully adjustable based on the device-specific design of the imaging device. The BIO instrument illumination height adjustment knobs and instrument illumination adjustment levers 8500 remain unobstructed and accessible.

Figure 9:
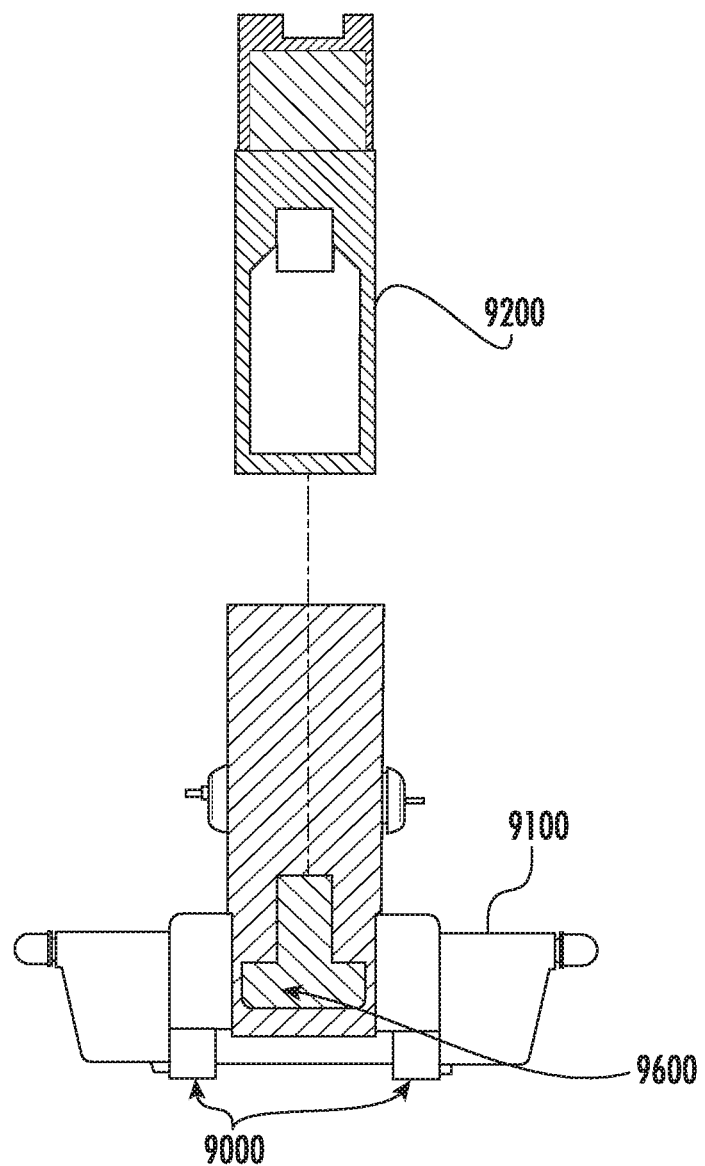
FIG. 9 is a schematic diagram of a depiction of one possible embodiment of the device taught herein, including the BIO, mounting bracket, and optional optical cartridge.

FIG. 9 shows a front-facing view of the BIO augmented imaging adapter assembly, including a BIO 9100, BIO viewport 9600, front-mounted mounting bracket 9000, and optical cartridge 9200. The mounting bracket, as explained, may be coupled or decoupled from the BIO viewport, and the optional optical cartridge may be removed from the mounting bracket, or it may be attached, integrated, or molded as one with the mounting bracket. In this depiction, the optional optical cartridge has been removed from the mounting bracket and separated; in embodiments, the cartridge will be optionally removable (either for ease of manufacturing and assembly, or by the end user), such as by sliding out of the mounting bracket. This removability allows for maintenance, repair and replacement, ease of access to replacement parts, updates, charging, switching in and out components, such as the camera, microprocessor, antenna, battery, and or sensor array, and/or repairing or otherwise manipulating components.

Figure 10:
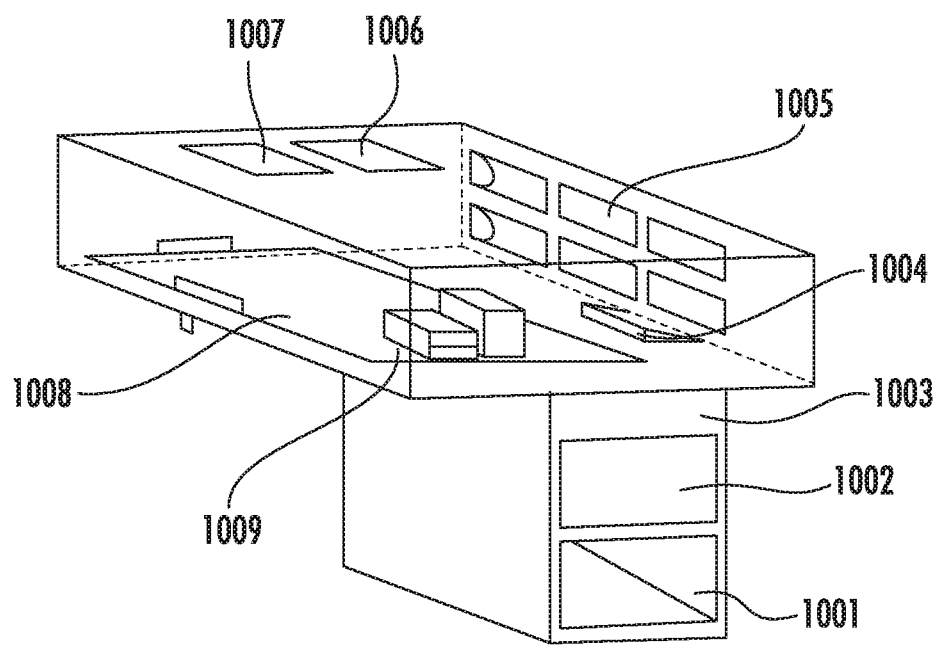
FIG. 10 is a schematic diagram of a depiction of one possible embodiment of the device taught herein.

FIG. 10 is a schematic diagram of the optical cartridge component assembly focusing on the computational, power, and data storage elements. The optical transmission window 1001 houses the beamsplitter. The illumination source window 1002 allows for transmission of light from the BIO illumination source. The camera and optical elements 1003 are contained in the optional cartridge as depicted. The component assembly also includes a power regulator and/or charger, 1004 as well as a battery or other power source 1005. It may include a charging port 1006 and possibly a removable storage device port 1007. The cartridge may include a microprocessor 1008, sensor array 1009, and/or antenna 1009.

Figure 11:
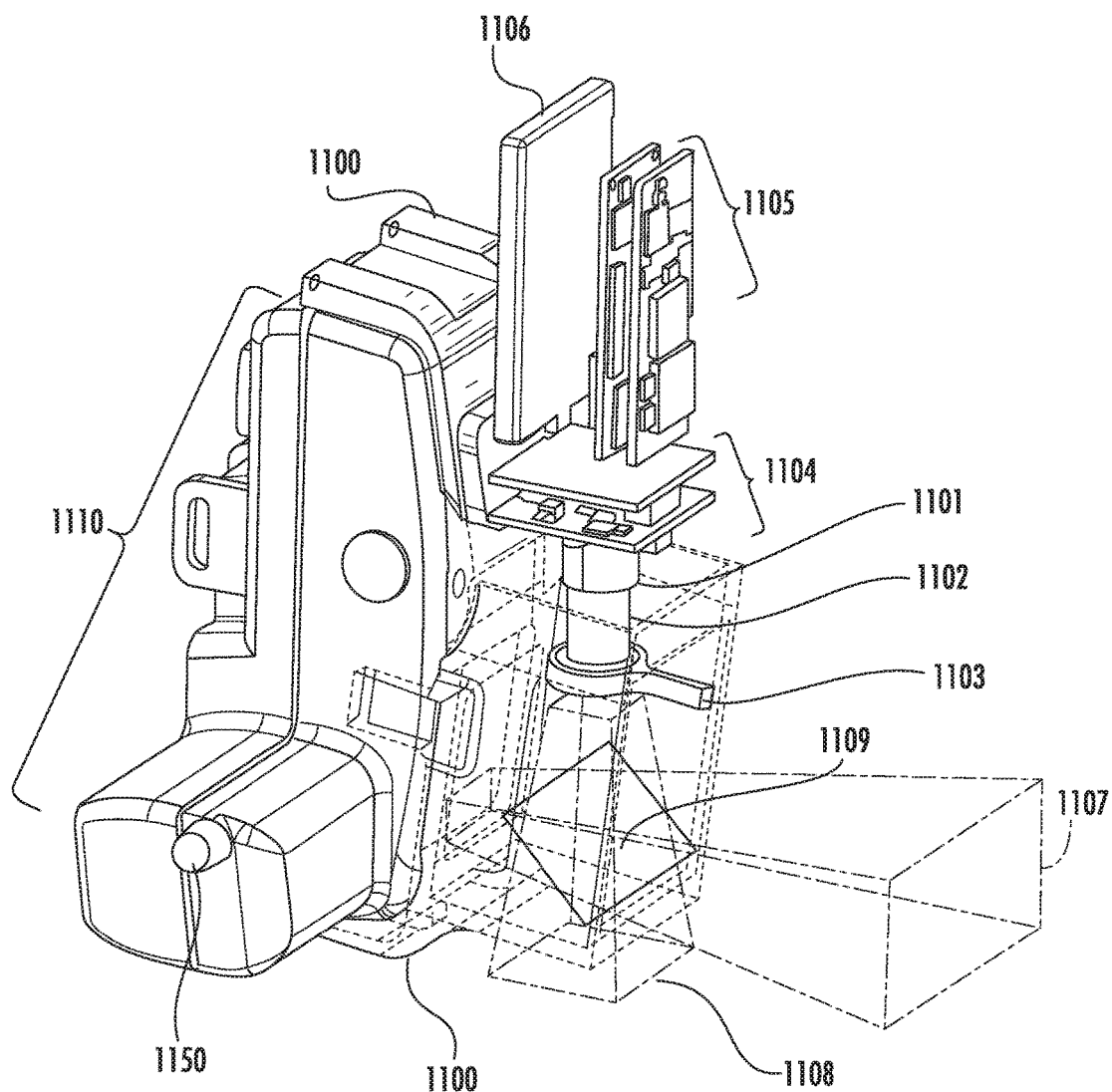
FIG. 11 is a schematic diagram of a depiction of one possible embodiment of the device taught herein, including the BIO, mounting bracket, and optional optical cartridge.

FIG. 11 is three-quarters view of the BIO augmented imaging adapter assembly, including the BIO 1110, front-mounted bracket assembly 1100, beamsplitter 1109, one or more camera 1101, camera lens 1102, and focus adjustment lever 1103, image sensor(s) and image coprocessor(s) 1104, the microprocessor and other electronic component(s) and/or controller(s) 1105, and the battery 1106. Adjustment knobs and levers 1150 on the existing BIO device are unobstructed by the mounting adapter design in preferred embodiments, allowing for full functionality of the device as familiar by examiners.

This diagram further demonstrates the correspondence between the field of view and angle of view between the BIO viewport and optical system (what the examiner sees) and the imaging device optical system (what the camera sees) as configured in the optical system of the optional optical cartridge (not depicted). For example, 1107 shows the viewing angle and field of view from the BIO viewport that shows the area that can be seen while examining the eye, which is what the examiner sees. 1108 shows the viewing angle and field of view of the camera system, which is positioned and configured so as to correspond to the reflected image of the eye under examination as view through the BIO viewport.

FIG. 12 is side-facing, cutaway diagram of the BIO augmented imaging adapter assembly, including the BIO 1210, front-mounted bracket assembly 1200, beamsplitter 1209, one or more camera 1201, camera lens 1202, and focus adjustment lever 1203, image sensor(s) and image coprocessor(s) 1204, the microprocessor and other electronic component(s) and/or controller(s) and sensor and network/antenna array 1205, and the battery 1206. Adjustment knobs and levers 1250 on the existing BIO device are unobstructed by the mounting adapter design in preferred embodiments, allowing for full functionality of the device as familiar by examiners.

This diagram further demonstrates the correspondence between the field of view and angle of view between the BIO viewport and optical system (what the examiner sees) and the imaging device optical system (what the camera sees) as configured in the optical system of the optional optical cartridge (not depicted). For example, 1207 shows the viewing angle and field of view from the BIO viewport that shows the area that can be seen while examining the eye, which is what the examiner sees. 1208 shows the viewing angle and field of view of the camera system, which is positioned and configured so as to correspond to the reflected image of the eye under examination as view through the BIO viewport.

One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. An imaging device for a binocular indirect ophthalmoscope, comprising:
   one or more camera, wherein the one or more camera is optionally provided by a cartridge comprising the one or more camera;
   a mounting bracket capable of removably attaching the one or more camera or the cartridge to a binocular indirect ophthalmoscope;
   wherein the mounting bracket comprises an opening or window configured such that when the mounting bracket is attached to the one or more camera or cartridge and to the binocular indirect ophthalmoscope, the opening or window permits incident light from an eye or portion of an eye being examined to transmit to a patient-facing front viewport of the binocular indirect ophthalmoscope;

one or more computer processing unit, memory unit, and/or communication device for sending one or more electronic still and/or video images from the one or more camera to an electronic device by way of a wired or wireless connection and/or for storing the one or more electronic still and/or video images on the one or more memory unit;

a beamsplitter, wherein the incident light from the eye or portion of the eye being examined is partially transmitted to the patient-facing front viewport or a front viewing window of the binocular indirect ophthalmoscope and partially directed to the one or more camera; and a power source.

2. The imaging device of claim 1, wherein the mounting bracket comprises an opening or window configured such that when the mounting bracket is attached to the one or more camera or cartridge and to the binocular indirect ophthalmoscope, the opening or window permits transmission of light from an illumination source of the binocular indirect ophthalmoscope.

3. The imaging device of claim 1, wherein the one or more computer processing unit, memory unit, and/or communication device is capable of sending and/or receiving information associated with the one or more electronic still and/or video images.

4. The imaging device of claim 3, wherein the one or more communication device enables bi-directional networked image or video capture, redisplay, control, and/or transmission of the one or more electronic still and/or video images and/or associated data.

5. The imaging device of claim 3, wherein the one or more communication device enables bi-directional networked automation of:
filing and/or organization of the one or more electronic still and/or video images; and/or
association of the one or more electronic still and/or video images with a specific patient(s), an examining physician(s), date(s) of an examination(s), specific ocular feature(s) detected by the device, specific device(s) used, image quality data, operational data of the device(s), and/or location(s) of the device(s) or examination(s).

6. The imaging device of claim 1, wherein the mounting bracket is removably attached to the binocular indirect ophthalmoscope using one or more of the following:
a. a bracket mechanism,
b. a sliding mechanism,
c. a clip mechanism,
d. an expansion joint mechanism,
e. tension spring(s),
f. magnets(s),
g. fastening tab(s),
h. interlocking component assembly,
i. molded-fit assembly,
j. press-on assembly,
k. hook-and-eyelet,
l. snap fastener(s),
m. snap-fit joint(s),
n. removable adhesive,
o. interlocking joint(s),
p. snap-on joining mechanism,
q. cantilever joining mechanism,
r. U-shaped, torsional, and/or annular snap-fit joining assembly techniques, and/or
s. mechanisms in which a protruding part of one component is deflected during a joining operation and catches in a depression in a mating component.

7. The imaging device of claim 1, wherein removably attaching the mounting bracket to the binocular indirect ophthalmoscope does not require disassembling or altering of the binocular indirect ophthalmoscope.

8. The imaging device of claim 1, wherein the electronic device or a remote device allows for altering settings on and/or operation of the imaging device, controlling the imaging device, and/or triggering capture of the one or more electronic still and/or video images.

9. The imaging device of claim 1, wherein the beamsplitter is a linear plate beamsplitter.

10. The imaging device of claim 1, wherein the beamsplitter is capable of producing a singly reflected image of an eye or structures within an eye under examination.

11. The imaging device of claim 1, wherein light from an eye under examination passes through the beamsplitter and to a single triangular mirror block associated with an optical system of the binocular indirect ophthalmoscope.

12. The imaging device of claim 1, further comprising a sensor array.

13. The imaging device of claim 1, further comprising a footswitch controller to trigger capturing the one or more electronic still and/or video images using the one or more camera.

14. The imaging device of claim 1, wherein the electronic device is chosen from a phone, computer, tablet computer, server, laptop computer, television, monitor, sensor, computer processing unit, and/or Internet-, local area network-, or wide area network-connected device.

15. The imaging device of claim 1, wherein the electronic device is used to perform one or more of the following tasks:
a. control settings on or related to the imaging device;
b. to operate the imaging device;
c. to redisplay the one or more electronic still and/or video images captured from the imaging device; and/or
d. to transmit, receive, analyze, gather, or collect information associated with the imaging device and/or the one or more electronic still and/or video images captured from the imaging device.

16. The imaging device of claim 1, wherein the one or more still and/or video images are processed by locally stored computer software applications, computer software applications stored remotely on a separate networked device(s), or computer software applications stored on a remote server(s).

17. The imaging device of claim 1, wherein the one or more camera provides an extended focal plane and/or field of view and is capable of capturing the one or more still and/or video images corresponding to portions of a human or animal eye as viewed by a user of the binocular indirect ophthalmoscope.

18. The imaging device of claim 1, wherein the mounting bracket is capable of positioning the one or more camera or cartridge on a patient-facing side of the binocular indirect ophthalmoscope.

19. The imaging device of claim 1, wherein the one or more camera is positioned above and between the eyepieces of the binocular indirect ophthalmoscope, and wherein the one or more camera is mounted centrally or paracentrally to incident light beams in a visual axis of the binocular indirect ophthalmoscope.

20. The imaging device of claim 1, further comprising a lens or combination of lenses having an f-number greater than f−1.8.

21. The imaging device of claim 1, wherein the mounting bracket is aligned flush with a patient-facing viewport on the binocular indirect ophthalmoscope.

22. The imaging device of claim 1, wherein the mounting bracket allows access to and operability of adjustment knobs or levers on the binocular indirect ophthalmoscope.

23. The imaging device of claim 22, wherein the adjustment knobs or levers on the binocular indirect ophthalmoscope allow for adjusting one or more of:
   a. interpupillary distance;
   b. transmission and/or manipulation of the illumination source of the binocular indirect ophthalmoscope;
   c. instrument illumination intensity, aperture, and/or angle of the binocular indirect ophthalmoscope;
   d. optical alignment;
   e. stereopsis;
   f. viewing angle; and/or
   g. position of the binocular indirect ophthalmoscope on a user's head.

24. The imaging device of claim 1, wherein the one or more computer processing unit allows for optical- and/or sensor-assisted algorithmic techniques chosen from one or more of the following:
   a. focus stacking;
   b. inverting or reorienting the one or more electronic still and/or video images;
   c. removing or reducing glare or visual occluding elements from the electronic still and/or video images;
   d. automatic capturing of the one or more electronic still and/or video images when a retina, an optic nerve, and/or other portion of an eye is detected and in focus;
   e. comparing the one or more electronic still and/or video images captured by the one or more camera with a library of images to detect which eye is being examined, detect an optic nerve, retinal vasculature, macula, or retinal periphery, and/or detect abnormal features of an eye being examined;
   f. software-selectable focusing planes;
   g. expanded depth of field imaging;
   h. region of interest-based focusing;
   i. exposure and focus controlling to ensure proper focus and exposure without or with minimal user intervention in routine clinical examination settings;
   j. construction of a 3-dimensional view(s) of an eye and/or ocular structure;
   k. construction of a high dynamic range image(s) of an eye and/or ocular structure;
   l. automatic montaging of overlapping adjacent electronic still and/or video images for more complete representation of a retina, fundus, and/or other portion of an eye; and/or
   m. electronic annotation of observations.

25. The imaging device of claim 1, further comprising components communicating visual and/or nonvisual ambient notifications to a user of the binocular indirect ophthalmoscope chosen from one or more of visual cues, audio cues, and/or haptic feedback.

26. The imaging device of claim 1, further comprising:
   a first linear polarizer to polarize outgoing illumination from the illumination source of the binocular indirect ophthalmoscope through the opening or window in the mounting bracket; and
   a second linear polarizer to polarize incoming light to the one or more camera.

27. A method of examining an eye of a human or animal, comprising:
   providing a fundus camera operably connected to one or more sensor and one or more processor;
   providing a binocular indirect ophthalmoscope removably attached to the fundus camera, wherein a user of the binocular indirect ophthalmoscope has the ability to examine a patient's eye through the binocular indirect ophthalmoscope while simultaneously capturing one or more still and/or video images of the patient's eye or portion of the patient's eye to be viewed in real-time or at a later time;
   electronically and automatically collecting information associated with an eye examination, the eye being examined, the patient being examined, and/or an examiner examining the patient's eye;
   electronically and automatically integrating and correlating the information associated with the eye examination, the eye being examined, the patient being examined, and/or the examiner examining the patient's eye and the one or more still and/or video images of the patient's eye or portion of the patient's eye; and
   electronically transmitting the integrated and correlated information associated with the eye examination, the eye being examined, the patient being examined, and/or the examiner examining the patient's eye and the one or more still and/or video images of the patient's eye or portion of the patient's eye to an electronic device.

28. The method of claim 27, further comprising using the integrated information associated with the eye examination, the eye being examined, the patient being examined, and/or the examiner examining the patient's eye and the one or more still and/or video images of the patient's eye or portion of the patient's eye to perform one or more of the following:
   diagnose the patient;
   treat the patient;
   schedule other examinations or appointments;
   communicate with the patient, the examiner, or third parties; and/or
   create a database or library of all or part of the integrated information associated with the eye examination, the eye being examined, the patient being examined, and/or the examiner examining the patient's eye and the one or more still and/or video images of the patient's eye or portion of the patient's eye.

29. The method of claim 27, wherein the electronic device is chosen from a phone, computer, tablet computer, server, laptop computer, television, monitor, sensor, computer processing unit, and/or Internet-, local area network-, or wide area network-connected device.

30. The method of claim 27, wherein the fundus camera is attached to a mounting bracket, the mounting bracket being removably attached to a binocular indirect ophthalmoscope.

* * * * *